(12) United States Patent
Covalin et al.

(10) Patent No.: US 12,029,893 B1
(45) Date of Patent: Jul. 9, 2024

(54) WEARABLE AURICULAR NEUROSTIMULATOR AND METHODS OF USE

(71) Applicant: Spark Biomedical, Inc., Dallas, TX (US)

(72) Inventors: Alejandro Covalin, Los Angeles, CA (US); Jared Wettenstein, League City, TX (US)

(73) Assignee: Spark Biomedical, Inc., Dallas, TX (US)

( * ) Notice: Subject to any disclaimer, the term of this patent is extended or adjusted under 35 U.S.C. 154(b) by 0 days.

(21) Appl. No.: 18/209,852

(22) Filed: Jun. 14, 2023

(51) Int. Cl.
*A61N 1/04* (2006.01)

(52) U.S. Cl.
CPC ......... *A61N 1/0456* (2013.01); *A61N 1/0472* (2013.01)

(58) Field of Classification Search
None
See application file for complete search history.

(56) References Cited

U.S. PATENT DOCUMENTS

| | | | |
|---|---|---|---|
| 4,014,323 | A | 3/1977 | Gilmer et al. |
| 1,690,144 | A | 9/1987 | Rise et al. |
| 4,865,048 | A | 9/1989 | Eckerson |
| 4,966,164 | A | 10/1990 | Colsen et al. |
| 5,514,175 | A | 5/1996 | Kim et al. |
| 5,593,432 | A | 1/1997 | Crowther et al. |
| 6,567,702 | B1 | 5/2003 | Nekhendzy et al. |
| 6,697,670 | B2 | 2/2004 | Chomenky et al. |
| 7,797,042 | B2 | 9/2010 | Dietrich et al. |
| 7,856,275 | B1 | 12/2010 | Paul |
| 7,986,996 | B2 | 7/2011 | Bell |
| 8,204,601 | B2 | 6/2012 | Moyer et al. |
| 8,506,469 | B2 | 8/2013 | Dietrich et al. |
| 8,554,324 | B2 | 10/2013 | Brocke |
| 8,666,502 | B2 | 3/2014 | Hartlep et al. |

(Continued)

FOREIGN PATENT DOCUMENTS

| | | |
|---|---|---|
| WO | 2015109018 | 7/2015 |
| WO | 2015179571 | 11/2015 |
| WO | 2021011165 | 1/2021 |

OTHER PUBLICATIONS

Sailer, et al., Altered reward processing in the nucleus accumbens and mesial prefrontal cortex of patients with posttraumatic stress disorder, Neuropsychologia, 46:11, May 2008, pp. 2836-2844, DOI: 10.1016/j.neuropsychologia.2008.05.022.

(Continued)

*Primary Examiner* — Eric D. Bertram
(74) *Attorney, Agent, or Firm* — Finch & Maloney PLLC

(57) ABSTRACT

In an illustrative embodiment, a wearable auricular stimulator includes a flexible body adapted to be worn at least partially around an auricle of a wearer, including an exterior for positioning in contact with a wearer's skin, and an interior for supporting a three-dimensional (3D) circuitry layout, including traces deposited on surfaces of the interior of the flexible body, electrodes for delivering electrical stimulation therapy to the wearer via a skin-facing side of the flexible body, and electronic component(s) electrically connected with the electrodes and the traces, the electronic components including a processing circuitry element for delivering electrical stimulation treatment(s) via the electrodes.

20 Claims, 24 Drawing Sheets

(56) References Cited

U.S. PATENT DOCUMENTS

| | | | |
|---|---|---|---|
| 8,688,239 B2 | 4/2014 | Hartlep et al. | |
| 8,700,163 B2 | 4/2014 | Terry, Jr. et al. | |
| 8,751,020 B2 | 6/2014 | Beck et al. | |
| 8,755,892 B2 | 6/2014 | Amurthur et al. | |
| 8,885,861 B2 | 11/2014 | Beck et al. | |
| 8,918,178 B2 | 12/2014 | Simon et al. | |
| 8,942,814 B2 | 1/2015 | Szeles | |
| 8,965,518 B1 | 2/2015 | Ellrich et al. | |
| 9,014,811 B2 | 4/2015 | Pal et al. | |
| 9,089,691 B2 | 7/2015 | Libbus et al. | |
| 9,089,719 B2 | 7/2015 | Simon et al. | |
| 9,101,766 B2 | 8/2015 | Nekhendzy | |
| 9,216,290 B2 | 12/2015 | Terry, Jr. et al. | |
| 9,314,611 B2 | 4/2016 | Zschaeck et al. | |
| 9,415,220 B1 | 8/2016 | Spinelli et al. | |
| 9,662,269 B2 | 5/2017 | Brown et al. | |
| 9,782,584 B2 | 10/2017 | Cartledge et al. | |
| 9,839,577 B2 | 12/2017 | Brown et al. | |
| 1,002,254 A1 | 7/2018 | Pfeifer | |
| 10,010,479 B2 | 7/2018 | Brown et al. | |
| 10,058,478 B2 | 8/2018 | Schnetz et al. | |
| 10,130,809 B2 | 11/2018 | Cartledge et al. | |
| 10,155,114 B2 | 12/2018 | De Ridder | |
| 10,213,601 B2 | 2/2019 | Simon et al. | |
| 10,279,178 B2 | 5/2019 | Cartledge et al. | |
| 10,293,161 B2 | 5/2019 | Charlesworth et al. | |
| 10,322,062 B2 | 6/2019 | Brown et al. | |
| 10,413,719 B2 | 9/2019 | Brown et al. | |
| 10,426,945 B2 | 10/2019 | Tyler et al. | |
| 10,485,972 B2 | 11/2019 | Pal et al. | |
| 10,695,568 B1* | 6/2020 | Covalin | A61H 39/002 |
| 10,780,264 B2 | 9/2020 | Alam | |
| 10,828,461 B2 | 11/2020 | Cartledge et al. | |
| 10,857,360 B2 | 12/2020 | Waclawik | |
| 10,967,182 B2* | 4/2021 | Khodaparast | A61N 1/0492 |
| 11,235,148 B2 | 2/2022 | Charlesworth et al. | |
| 11,351,370 B2* | 6/2022 | Covalin | A61N 1/36028 |
| 11,623,088 B2 | 4/2023 | Covalin et al. | |
| 2005/0165460 A1 | 7/2005 | Erfan | |
| 2006/0064139 A1 | 3/2006 | Chung et al. | |
| 2007/0250145 A1 | 10/2007 | Kraus et al. | |
| 2008/0021517 A1 | 1/2008 | Dietrich | |
| 2008/0021520 A1 | 1/2008 | Dietrich | |
| 2008/0051852 A1 | 2/2008 | Dietrich et al. | |
| 2008/0249594 A1 | 10/2008 | Dietrich et al. | |
| 2009/0287035 A1 | 11/2009 | Dietrich et al. | |
| 2010/0057154 A1 | 3/2010 | Dietrich et al. | |
| 2010/0222843 A1 | 9/2010 | Tass et al. | |
| 2010/0262205 A1 | 10/2010 | De Ridder | |
| 2011/0166624 A1* | 7/2011 | Dietrich | A61N 1/0472 607/57 |
| 2013/0079862 A1 | 3/2013 | Ellrich | |
| 2013/0150923 A1 | 6/2013 | Schnetz et al. | |
| 2013/0231729 A1 | 9/2013 | Hartlep et al. | |
| 2013/0231730 A1 | 9/2013 | Hartlep et al. | |
| 2014/0046406 A1 | 2/2014 | Ellrich et al. | |
| 2014/0121740 A1 | 5/2014 | Patterson et al. | |
| 2014/0126752 A1* | 5/2014 | Beck | A61N 1/36036 381/151 |
| 2014/0135886 A1 | 5/2014 | Cook et al. | |
| 2014/0142669 A1 | 5/2014 | Cook et al. | |
| 2014/0316456 A1* | 10/2014 | Ando | A61H 7/004 606/204 |
| 2015/0018925 A1 | 1/2015 | Zschaek et al. | |
| 2015/0018926 A1 | 1/2015 | Frenkel et al. | |
| 2015/0080986 A9 | 3/2015 | Ellrich et al. | |
| 2015/0165195 A1 | 6/2015 | Hartlep et al. | |
| 2015/0174418 A1 | 6/2015 | Tyler et al. | |
| 2017/0224990 A1 | 8/2017 | Goldwasser | |
| 2017/0296807 A1 | 10/2017 | Brown et al. | |
| 2017/0368329 A1 | 12/2017 | Tyler et al. | |
| 2018/0085573 A1 | 3/2018 | Alam | |
| 2018/0200522 A1* | 7/2018 | Taca, Jr. | A61N 1/36089 |
| 2018/0296435 A1 | 10/2018 | Brown et al. | |
| 2018/0318585 A1 | 11/2018 | Pfeifer | |
| 2019/0046794 A1 | 2/2019 | Gooddall et al. | |
| 2019/0111259 A1 | 4/2019 | De Ridder | |
| 2019/0134390 A1 | 5/2019 | Shimada | |
| 2019/0262229 A1 | 8/2019 | Brown et al. | |
| 2019/0275322 A1 | 9/2019 | Cartledge et al. | |
| 2020/0030608 A1 | 1/2020 | Halpern | |
| 2020/0038658 A1 | 2/2020 | Tyler et al. | |
| 2020/0108250 A1 | 4/2020 | Ireland | |
| 2020/0139124 A1 | 5/2020 | Amurthur | |
| 2020/0197707 A1* | 6/2020 | Covalin | A61N 1/0456 |
| 2020/0238085 A1* | 7/2020 | Khodaparast | A61N 1/0492 |
| 2020/0261688 A1 | 8/2020 | Thoma | |
| 2020/0261722 A1 | 8/2020 | Alataris et al. | |
| 2020/0323684 A1 | 10/2020 | O'Leary et al. | |
| 2020/0345970 A1 | 11/2020 | La Rovere et al. | |
| 2021/0001124 A1* | 1/2021 | Brown | A61N 1/36 |
| 2021/0038879 A1 | 2/2021 | Pfeifer | |
| 2021/0069505 A1* | 3/2021 | Romine | A61N 1/0456 |
| 2021/0077812 A1 | 3/2021 | Hool et al. | |
| 2021/0213286 A1* | 7/2021 | Covalin | A61N 1/36036 |
| 2022/0168568 A1 | 6/2022 | Alataris et al. | |
| 2023/0026037 A1* | 1/2023 | Larraya | A61N 1/36034 |
| 2023/0138891 A1* | 5/2023 | Chan | B33Y 10/00 600/301 |
| 2023/0149703 A1 | 5/2023 | Covalin et al. | |

OTHER PUBLICATIONS

Neylan, Thomas C., Frontal Lobe Moderators and Mediators of Response to Exposure Therapy in PTSD, Am J Psychiatry, 174:12, Dec. 2017, pp. 1131-1133, DOI: 10.1176/appi.ajp.2017.17091056.

Mehta, et al., Inflammation, reward circuitry and symptoms of anhedonia and PTSD in trauma-exposed women, Social Cognitive and Affective Neuroscience, vol. 15, Issue 10, 2020, pp. 1046-1055, DOI: 10.1093/scan/nsz100.

Boukezzi, et al., Posttraumatic Stress Disorder is associated with altered reward mechanisms during the anticipation and the outcome of monetary incentive cues, NeuroImage: Clinical, vol. 25, 102073, 2020, DOI: 10.1016/j.nicl.2019.102073.

Sherin, Jonathan E., and Nemeroff, Charles B., Post-traumatic stress disorder: the neurobiological impact of psychological trauma, Dialogues in Clinical Neuroscience, vol. 13, No. 3, 2011, pp. 263-278.

Somohano, et al., PTSD symptom clusters and craving differs by primary drug of choice, J Dual Diagn., 15(4), 2019, pp. 233-242, DOI: 10.1080/15504263.2019.1637039.

Elman, et al., Reward and aversion processing in patients with post-traumatic stress disorder: functional neuroimaging with visual and thermal stimuli, Translational Psychiatry, 8:240, Nov. 2018, pp. 1-15, DOI: 10.1038/s41398-018-0292-6.

Seidemann, et al., The Reward System and Post-Traumatic Stress Disorder: Does Trauma Affect the Way We Interact With Positive Stimuli?, Chronic Stress, vol. 5, Feb. 25, 2021, pp. 1-11, DOI: 10.1177/2470547021996006.

Torrisi, et al., Therapeutic Challenges of Post-traumatic Stress Disorder: Focus on the Dopaminergic System, Frontiers in Pharmacology, vol. 10, Article 404, Apr. 17, 2019, pp. 1-11, DOI: 10.3389/fphar.2019.00404.

Basner, et al., Continuous and Intermittent Artificial Gravity as a Countermeasure to the Cognitive Effects of 60 Days of Head-Down Tilt Bed Rest, Frontiers in Physiology, vol. 12, Article 643854, Mar. 17, 2021, pp. 1-14, DOI: 10.3389/fphys.2021.643854.

Jenkins, et al., Transcutaneous Auricular Neurostimulation (tAN): A Novel Adjuvant Treatment in Neonatal Opioid Withdrawal Syndrome, Frontiers in Human Neuroscience, vol. 15, Article 648556, Mar. 8, 2021, pp. 1-12, DOI: 10.3389/fnhum.2021.648556.

U.S. Department of Veterans Affairs, Pain Management Opioid Taper Decision Tool, A VA Clinician's Guide, Oct. 2016, IB 10-939 P96820.

Opioid Oral Morphine Milligram Equivalent (MME) Conversion Factors, Aug. 2017. Available at: https://www.cms.gov/Medicare/Prescription-Drug-coverage/PrescriptionDrugCovContra/Downloads/Opioid-Morphine-EQ-Conversion-Factors-Aug-2017.pdf.

U.S. Department of Health and Human Services, Centers for Disease Control and Prevention, Calculating Total Daily Dose of

(56) References Cited

OTHER PUBLICATIONS

Opioids for Safer Dosage. Available at: https://www.cdc.gov/drugoverdose/pdf/calculating_total_daily_dose-a.pdf.
Extended European Search Report dated Aug. 4, 2022 in related European Application No. 20840682.7, 7 pages.
Non-Final Office Action dated Jun. 3, 2021 for U.S. Appl. No. 17/219,712, 28 pages.
Final Office Action dated Sep. 16, 2021 for U.S. Appl. No. 17/219,712, 14 pages.
Notice of Allowance dated Jan. 26, 2022 for U.S. Appl. No. 17/219,712, 8 pages.
Filippelli, et al., Non-insertive Acupuncture and Neonatal Abstinence Syndrome: A Case Series From an Inner-city Safety Net Hospital, Global Advances in Health and Medicine, vol. 1, No. 4, Sep. 2012, pp. 48-52.
Raith, et al., Laser Acupuncture as An Adjuvant Therapy for a Neonate with Neonatal Abstinence Syndrome (nas) Due to Maternal Substitution Therapy: Additional Value of Acupuncture, Acupuncture in Medicince, vol. 32, Issue 6, Dec. 1, 2014, pp. 523-524.
Han, et al., Mobilization of Specific Neuropeptides by Peripheral Stimulation of Identified Frequencies, Physiology, vol. 7, Issue 4, Aug. 1, 1992, pp. 176-180.
Han, Ji-Sheng, Acupuncture and Endorphins, Neuroscience Letters, No. 361, 2004, pp. 258-261.
Meade, et al., A Randomized Trial Of Transcutaneous Electric Acupoint Stimulation As Adjunctive Treatment For Opiod Detoxification, Journal of Substance Abuse Treatment, vol. 38, Issue 1, Jan. 2010, pp. 12-21.
Cioca, et al., A Correlation Between GDV And Heart Rate Variability Measures: A New Measure Of Well Being, Measuring Energy Fields: Current Research, 2004, Backbone Publishing Co. Fair Lawn, USA, pp. 59-64.
Goldstein, Daniel R., Aging, Imbalanced Inflammation And Viral Infection, Virulence, vol. 1, Issue 4, Jul./Aug. 2010, Landes Bioscience, pp. 295-298.
AHRQ Safety Program For Mechanically Ventilated Patients Final Report, Prepared by Johns Hopkins Medicine Armstrong Institute for Patient Safety and Quality, Jan. 2017.
Jdupa, et al., Alteration Of Cardiac Autonomic Functions In Patients With Major Depression; A Study Using Heart Rate Variability Measures, Journal of Affective Disorders 100, 2007, pp. 137-141.
Freed, et al., Antiviral Innate Immunity: Editorial Overview, Journal of Molecular Biology, vol. 426, Issue 6, Mar. 20, 2014, pp. 1129-1132.
Mercante, et al., Aurical Neuromodulation: The Emerging Concept Beyond The Stimulation Of Vagus And Trigeminal Nerves, Medicines, vol. 5, Issue 1, Jan. 21, 2018, article No. 10.
Barnes, Peter J., Autonomic Control Of The Lower Airways, Primer on the Autonomic Nervous System (Third Edition), 2012, pp. 201-204.
Vaillancourt, et al., Autonomic Nervous System Involvement In Pulmonary Arterial Hypertension, Respiratory Research 18, Dec. 4, 2017, article No. 201.
Astrup, et al., Cardiac Autonomic Neuropathy Predicts Cardiovascular Morbidity And Mortality In Type 1 Diabetic Patients With Diabetic Nephropathy, Diabetes Care, vol. 29, Issue 2, Feb. 1, 2006, pp. 334-339.
Pavlov, et al., Controlling Inflammation: The Cholinergic Anti-Inflammatory Pathway, Biochemical Society Transactions, vol. 34, Part 6, Oct. 25, 2006, pp. 1037-1040.
Mehta, et al., COVID-19: Consider Cytokine Storm Syndromes And Immunosuppression, The Lancet, vol. 395, Issue 10229, Mar. 16, 2020, pp. 1033-1034.
Stebbing, et al., COVID-19: Combining Antiviral And Anti-Inflammatory Treatments, The Lancet Infectious Diseases, vol. 20, No. 4, Feb. 27, 2020, pp. 400-402.
Oke, et al., From CNI-1493 To The Immunological Homunculus: Physiology of The Inflammatory Reflex, Journal of Leukocyte Biology, vol. 83, Issue 3, Dec. 7, 2007, pp. 512-517.
Boman, Kajsa, Heart Rate Variability A Possible Measure Of Subjective Wellbeing?, University of Skövde Bachelor Degree Project in Cognitive Neuroscience, 2018.
Young, et al., Heart-Rate Variability: A Biomarker To Study The Influence Of Nutrition On Physiological And Psychological Health?, Behavioural Pharmacology, vol. 29, Issue 2, Mar. 15, 2018, pp. 140-151.
Aguilera, et al., Inflammation As A Modulator Of Host Susceptibility To Pulmonary Influenza, Pneumococcal, And Co-Infections, Frontiers In Immunology, vol. 11, Feb. 11, 2020, article No. 105.
Krygier, et al., Mindfulness Meditation, Well-Being, And Heart Rate Variability: A Preliminary Investigation Into The Impact Of Intensive Vipassana Meditation, International Journal of Pyschophysiology, vol. 89, Issue 3, Sep. 2013, pp. 305-313.
Chiluwal, et al., Neuroprotective Effects Of Trigeminal Nerve Stimulation In Severe Traumatic Brain Injury, Scientific Reports, vol. 7, Jul. 28, 2017, article No. 6792.
Cohen, et al., Power Spectrum Analysis And Cardiovascular Morbidity In Anxiety Disorders, Autonomic Neuroscience, vol. 128, Issues 1-2, Jul. 30, 2006, pp. 1-8.
De Godoy, et al., Preoperative Nonlinear Behavior In Heart Rate Variability Predicts Morbidity And Mortality After Coronary Artery Bypass Graft Surgery, Medical Science Monitor, vol. 15, Issue 3, Feb. 21, 2009, pp. CR117-CR122.
Pavlov, et al., The Cholinergic Anti-Inflammatory Pathway, Brain, Behavior, and Immunity, vol. 19, Issue 6, May 26, 2005, pp. 493-499.
Pavlov, et al., The Cholinergic Anti-Inflammatory Pathway: A Missing Link In Neuroimmunomodulation, Molecular Medicine, vol. 9, No. 5-8, Jun. 30, 2003, pp. 125-134.
Yamada, et al., The Cholinergic Anti-Inflammatory Pathway: An Innovative Treatment Strategy For Respiratory Diseases And Their Comorbidities, Current Opinion in Pharmacology, vol. 40, Jan. 12, 2018, pp. 18-25.
Geisler, et al., The Impact Of Heart Rate Variability On Subjective Well-Being Is Mediated By Emotion Regulation, Personality and Individual Differences, vol. 49, Issue 7, Jul. 9, 2010, pp. 723-728.
Seifert, Hilary, The Inflammatory Response Initiated By The Spleen To Ischemic Stroke, University of South Florida Graduate Theses and Dissertations, Jan. 2013.
Nuntaphum, et al., Vagus Nerve Stimulation Exerts Cardioprotection Against Myocardial Ischemia/Reperfusion Injury Predominantly Through Its Efferent Vagal Fibers, Basic Research In Cardiology, vol. 113, May 9, 2018, article No. 22.
Non-Final Office Action dated Sep. 4, 2019 for U.S. Appl. No. 16/510,930.
Notice of Allowance dated Apr. 30, 2020 for U.S. Appl. No. 16/510,930.
International Search Report and Written Opinion for International Application No. PCT/US2020/039424 dated Sep. 9, 2020.
Non-Final Office Action dated May 15, 2020 for U.S. Appl. No. 16/846,220, 10 pages.
Notice of Allowance dated Nov. 27, 2020 for U.S. Appl. No. 16/846,220, 7 pages.
Janes, et al., An Increase in Tobacco Craving Is Associated with Enhanced Medial Prefrontal Cortex Network Coupling, PLOS One, vol. 9, Issue 2: e88228, Feb. 2014, pp. 1-5, DOI:10.1371/journal.pone.0088228.
Hayashi, et al., Dorsolateral prefrontal and orbitofrontal cortex interactions during self-control of cigarette craving, Proceedings of the National Academy of Sciences of the United States of America, vol. 110, No. 11, Mar. 12, 2013, pp. 4422-4427, DOI: 10.1073/pnas/1212185110.
Karkhanis, et al., Dynorphin/Kappa Opioid Receptor Signaling in Preclinical Models of Alcohol, Drug, and Food Addiction, International Review of Neurobiology, Jan. 2017, pp. 1-36, DOI: 10.1016/bs.im.2017.08.001.
Gottfried, et al., Encoding Predictive Reward Value in Human Amygdala and Orbitofrontal Cortex, Science Mag., vol. 301, Issue 5636, Aug. 22, 2003, pp. 1104-1107, DOI: 10.1126/science.1087919.
Alizadehgoradel, et al., Repeated stimulation of the dorsolateral-prefrontal cortex improves executive dysfunctions and craving in

(56) References Cited

OTHER PUBLICATIONS drug addiction: A randomized, double-blind, parallel-group study, Brain Stimulation, vol. 13, Issue 3, Jan. 5, 2020, pp. 582-593, DOI: 10.1016/j.brs.2019.12.028.

Altshuler, et al., Role of orbitofrontal cortex in incubation of oxycodone craving in male rats, Addiction Biology, Jun. 22, 2020, vol. 26, Issue 2, e12927, pp. 1-11, DOI: 10.1111/adb. 12927.

Li, et al., The Central Amygdala Nucleus is Critical for Incubation of Methamphetamine Craving, Neuropsychopharmacology, vol. 40, Jan. 7, 2015, pp. 1297-1306, DOI: 10.1038/npp.2014.320.

Childs, et al., Vagus nerve stimulation reduces cocaine seeking and alters plasticity in the extinction network, Cold Spring Harbor Laboratory Press, vol. 24, 2016, pp. 35-42, DOI: 10.1101/lm.043539.116.

Bloom, et al., Neurons containing beta endorphin in rat brain exist separately from those containing enkephalin: Immunocytochemical studies, Proc. Natl. Acad. Sci. USA, vol. 75, No. 3, Mar. 1978, pp. 1591-1595.

Tilbrook, AJ, Neuropeptides, Stress-Related, Encyclopedia of stress, vol. 2, 2007, pp. 903-908.

Hutson, et al., Region-Specific Contribution of the Ventral Tegmental Area to Heroin-Induced Conditioned Immunomodulation, Brain Behav Immun., vol. 38, May 2014, pp. 118-124, DOI: 10.1016/j.bbi.2014.01.008.

Veening, Jan G., and Barendregt, Henk P., The effects of Beta-Endorphin: state change modification, Fluids and Barriers of the CNS, 12:3, Jan. 2015, pp. 1-22, DOI: 10.1186/2045-118-12-3.

Eisenstein, Toby K., The Role of Opioid Receptors in Immune System Function, Frontiers in Immunology, vol. 10, Article 2904, Dec. 20, 2019, DOI: 10.3389/fimmu.2019.02904.

Veening, et al., Volume transmission of beta-endorphin via the cerebrospinal fluid; a review, Fluids and Barriers of the CNS, 9:16, Aug. 2012, pp. 1-16, DOI: 10.1186/2045-8118-9-16.

\* cited by examiner

WEARABLE AURICULAR NEUROSTIMULATOR AND METHODS OF USE

BACKGROUND

Non-invasive, easy to use and/or apply medical therapies are the goal of novel non-pharmacological treatments. A prime example of these treatments are wearable medical devices. While a medical device has as its primary objectives to be safe and effective, the objectives of any wearable are comfort, ease of use, and aesthetics. These two sets of objectives are often difficult to align.

Devices for stimulation of neural structures on and surrounding a patient's ear have been designed for providing stimulation with and without piercing the dermal layers on or surrounding the ear. Non-piercing electrodes, for example, may be frictionally and/or adhesively retained against the skin on and surrounding the patient's ear to target various nerve structures. The non-piercing electrodes may have a substantial surface area in comparison to systems relying upon dermal-piercing electrodes, such that multiple nerve terminals are stimulated by a single electrode during therapy. A number of nerve terminals may be situated directly beneath and/or beneath and closely adjacent to the skin upon which the non-piercing electrode is positioned. By targeting multiple nerve terminals, positioning of each electrode does not necessarily need to be precise. Therefore, for example, a patient or caregiver may be able to apply and remove the device as desired/needed (e.g., for sleeping, showering, etc.). Further, targeting multiple nerve terminals is advantageous since stimulating multiple branches of a nerve elicits a stronger response than stimulating a single branch, which is the case when using pinpoint electrodes such as needle electrodes. Such devices, for example, are described in U.S. Pat. No. 10,695,568 entitled "Device and Method for the Treatment of Substance Use Disorders" and U.S. Pat. No. 11,623,088 entitled "Devices and Methods for the Treatment of Substance Use Disorders," each of which is incorporated by reference herein in its entirety.

The transdermal stimulation of these nerve regions enables a variety of beneficial treatments. In some examples, these include the treatment of acute or chronic pain, inflammatory conditions, and cognitive difficulties. The Nucleus of the solitary tract (NTS), for example, receives afferent connections from many areas including the Trigemino-cervical complex (TCC), the cervical vagus nerve as well as from the auricular branch of the vagus nerve (ABVN). The TCC is a region in the cervical and brain stem area where trigeminal and occipital fibers synapse, including the Auriculotemporal nerve (ATN), the lesser occipital nerve and the greater auricular nerve are located. The TCC projects to multiple areas in the brain stem including, but not limited to the Nucleus Raphe Magnus (NRM) as well as other parts of the Raphe nuclei (we refer to all of the particular Raphe nuclei as Raphe Nucleus (RN) herein), the Locus Coeruleus (LC), Periaqueductal Gray (PAG), Nucleus Basalis (NBM), the Nucleus Ambiguus (NA), the Ventral Tegmental Area (VTA), the Nucleus Accumbens (NAc), the NTS, and Parabrachial nucleus (PbN). The NTS, among others, also projects to the RN (e.g., NRM), the LC, and the PAG as well as to high centers like the hypothalamus, including into the Arcuate Nucleus (ARC) which receives its majority of non-intrahypothalamic afferents from the NTS. Additionally, many interconnections exist amongst different brainstem nuclei (e.g., PAG, LC, RN, NRM, NBM, PbN, PPN, NA, VTA, NAc); for example, the LC, PAG, and RN (e.g., NRM) project to the NA, and the PPN projects into the VTA. The VTA, in turn, projects to the Prefrontal Cortex, being interconnected with the hypothalamus and the hippocampus. The VTA projects directly to the Hippocampus as well. The Hippocampus, in turn, projects to the NAc and interconnects with the hypothalamus.

There are descending indirect connections going to the heart, lungs, gut, and spleen. Indirect connections include connections where there is at least one synapse elsewhere before reaching the target. This means that modulating the activity of these neural circuits can affect the respective organs. For example, heart rate can be modulated (e.g., heart rate can be decreased and heart rate variability can be increased); oxygen absorption can be increased at the lungs by increasing the compliance of the bronchi tissue and thus increasing the oxygen transport availability therefore increasing the potential for more oxygen to be absorbed into the blood; gut motility can be increased by descending pathways originating in the dorsal motor nucleus of the vagus nerve (DMV); since DMV activity is modulated by NTS activity, motility in the gut can be affected by modulating the activity in the NTS; and a decrease in circulating pro-inflammatory cytokines can be achieved by modulating spleen activity via NTS descending pathways. For examples of increasing bronchial compliance and decreasing inflammation, see U.S. Pat. No. 10,967,182 entitled "Devices and Methods for Reducing Inflammation Using Electrical Stimulation," incorporated by reference herein in its entirety. Additionally, modulating spleen activity can enhance platelet function allowing for a faster and more effective coagulation; one that can happen even with a deficiency in coagulation factors (e.g., hemophilia A, B, and C, Factor I, II, V, VII, X, XII, XIII deficiency) and/or in the presence of other coagulation deficiencies (e.g., Von Willebrand disease (VWD)).

Heart rate variability (HRV) is a reflection of the state of the autonomic nervous system (ANS). The sympathetic branch of the ANS, which is more active during stress situations tends to increase heart rate (HR) and decrease HRV; the opposite is true for the parasympathetic branch of the ANS, which tend to decrease HR and increase HRV. While lower HRV has been associated with morbidity and mortality in several conditions, higher HRV has been associated with well-being; thus, HRV has been used as a health biomarker. For examples of treating stress, see U.S. Patent Application Publication No. 2023/0149703 entitled "Devices and Methods for Treating Stress and Improving Alertness Using Electrical Stimulation," incorporated by reference herein in its entirety.

There are at least three different opioid receptors, Mu (μ), Delta (δ), and Kappa (κ), which amongst other things, can modulate pain, as well as directly and indirectly the production of important neuromodulators such as for example dopamine (DA), norepinephrine (NE), serotonin (5-HT), and acetylcholine (Ach). The body produces endogenous agonist peptides for each of these three opioid receptors. These peptides are called endorphins, which primarily binds to the Mu (μ) receptors, Enkephalin which primarily binds to the Delta (δ) receptors and to a lesser degree to the Mu (μ) receptors, and Dynorphins, which primarily binds to the Kappa (κ) receptors. Pain studies suggest that central production of these endogenous peptides follow different pathways. While enkephalin production is more distributed, production of endorphins is primarily mediated by activity in the Arcuate Nucleus (ARC) in the hypothalamus, and activity in the Parabrachial nucleus highly influences production of dynorphins. Neurostimulation therapy for pain modulation may be performed such that it mitigates or alleviates chronic, recurring, and/or acute pain. For example, apparatus described herein may be used to treat chronic back pain, headache, migraine, cluster headache, pain due to temporomandibular disorders (TMD), pain due to endometriosis, menstrual pain, and/or cramps (e.g., menstrual cramps, endometriosis, etc.).

Transdermal stimulation treatment devices can be used to induce neuronal plasticity or Neuroplasticity for provoking cognitive improvements, stroke recovery, post-traumatic stress disorder (PTSD), phobias, attention deficit/hyperactivity disorder (ADHD), attention deficit disorder (ADD), dementia including treating Alzheimer's disease. Neuroplasticity underlies learning; therefore, strategies that enhance neuroplasticity during training have the potential to greatly accelerate learning rates. Earlier studies have successfully demonstrated that invasive or implanted vagus nerve stimulation (VNS) can drive robust, specific neural plasticity. Brief bursts of VNS are paired with training to engage pro-plasticity neuromodulatory circuits and reinforce the specific neural networks that are involved in learning. The same can be achieved in a non-invasive manner; for example via stimulation of the ABVN as well as indirectly via stimulation of the ATN. This precise control of neuroplasticity, coupled with the flexibility to be paired with virtually any training paradigm, establishes the stimulation of any of these nerves as a potential targeted neuroplasticity training paradigm. For examples of treatment of cognitive disorders, see U.S. Pat. No. 11,351,370 entitled "Devices and Methods for Treating Cognitive Dysfunction and Depression Using Electrical Stimulation," incorporated by reference herein in its entirety. Another example is training to regain function after a stroke, which can be done with or without feedback. When feedback is used it is typically in the form of a triggering mechanism. The triggering mechanism, in some examples, could be a person/trainer observing the person training or a sensor such as a motion sensor, an accelerometer, EEG, EKG or EMG sensor, amongst others.

The vagus nerve is one of the longest cranial nerves and along its trajectory can be located adjacent to the carotid artery in the neck (i.e., cervical vagus). Direct stimulation of the vagus nerve activates the nucleus tractus solitarius (NTS), which has projections to nucleus basalis (NBM) and locus coeruleus (LC). The NBM and LC are deep brain structures that respectively release acetylcholine and norepinephrine, which are pro-plasticity neurotransmitters important for learning and memory. Stimulation of the vagus nerve using a chronically implanted electrode cuff is safely used in humans to treat epilepsy and depression and has shown success in clinical trials for tinnitus and motor impairments after stroke. For examples of treating depression, see U.S. Pat. No. 11,351,370 entitled "Devices and Methods for Treating Cognitive Dysfunction and Depression Using Electrical Stimulation."

The ABVN ascends adjacent to the ear canal and surfaces via the mastoid canaliculus (MsC, also referred to as Arnold's canal) on its way to innervate several dermatome regions of outer ear, for example, the cymba conchae as well as the interior part of the tragus. Non-invasive stimulation of the ABVN may drive activity in similar brain regions as invasive vagus nerve stimulation. Recently, auricular neurostimulation has proven beneficial in treating a number of human disorders.

Treatment devices can be designed to provide transdermal stimulation therapy to treat the same conditions that have been treated with implanted and percutaneous devices. Transdermal stimulation therapy can be designed to restore autonomic balance harmed, for example, by disorders such as cardiac heart failure, atrial fibrillation (AF), anxiety, stress, post-traumatic stress disorder (PTSD), gastric motility, depression, cluster headaches, migraines, inflammation and autoimmune disorders. Furthermore, these devices can also be designed to accelerate coagulation to stop bleeding faster, for example to help with chronic conditions such as in coagulation disorders; with periodic conditions, for example in cases of periodic heavy bleeding as in menorrhagia and/or heavy menstrual bleeding; as well as in acute scenarios as for example when bleeding after a traumatic event or to minimize bleeding in a surgical and post-surgical scenario. Transcutaneous electrical stimulation of the tragus (e.g., the anterior protuberance of the outer ear), which is partly enervated by the auricular branch of the vagus nerve, can elicit evoked potentials in the brainstem in human subjects. Based on these observations, it was demonstrated that atrial fibrillation inducibility was suppressed by transcutaneous low level-VNS stimulation, which was achieved through stimulation of the auricular branch of the vagus nerve at the tragus. Noninvasive transcutaneous low level-VNS stimulation increases AF threshold (mitigates risk of AF), as well as alleviates AF burden in mammals including humans. In healthy subjects, transcutaneous low level-VNS stimulation can also increase heart rate variability, increase parasympathetic tone, and/or reduce sympathetic outflow effectively restoring parasympathetic/sympathetic balance.

Transdermal stimulation therapy devices can be used to reduce inflammation caused by viral or bacterial infections as well as by other reasons. In the initial stages of infection, the body response includes the secretion of pro-inflammatory cytokines. In some cases, controlling this inflammatory response such that it can be reduced can help the body to heal faster. Inflammatory responses are a double-edged sword in the sense that it is necessary to eradicate cells infected by viruses as well as bacteria. However, an excessive pro-inflammatory response can actually lead to death. In particular in respiratory infections, pro-inflammatory cytokines may lead to an increase in pathogen replication. In addition, lung function may be compromised by the accumulation of pro-inflammatory cytokines. Studies suggest that the pro-inflammatory response in some individuals (e.g., older people) is often excessive. In many of these cases, it is this pro-inflammatory response that causes more harm than the infection itself resulting in the potential death of the infected subject. In response to Coronavirus Disease 2019 (COVID-19) and Severe Acute Respiratory Syndrome (SARS), for example, the human body produces an excessive pro-inflammatory response. In fact, evidence gathered so far suggests that in some individuals with severe COVID-19 the body responds by unleashing an exacerbated release of pro-inflammatory cytokines. Reducing the inflammatory response, e.g., through reducing circulating pro inflammatory cytokines, will, in some cases, reduce the time to heal and/or will reduce the time an infected person may need to use assistive respiratory therapy such as the need for a ventilator. In general, a patient stays on average less than 5 days on a ventilator; however, in the case of COVID-19, patients have been remaining on ventilators for as much as 3 or 4 times longer; i.e., 15 to 20 days. Healthcare centers are generally equipped with enough ventilators to serve a population that will need them in average less than 5 days. The increase in the time a ventilator is needed in COVID-19 patients is a factor in the overall mortality rate seen in COVID-19 since many patients in need of a ventilator will not have access to one. Via modulation of NTS activity, treatment devices and methods described herein can not only a) increase the compliance of the bronchi tissue ultimately providing more oxygen to the body but also, b) mitigate inflammation by reducing circulating pro-inflammatory cytokines in the body, including in the lungs. These two effects allow the novel treatment devices and methods described herein to behave as an adjuvant therapy in the treatment of respiratory infections (e.g., Middle East respiratory syndrome coronavirus (MERS), severe acute respiratory syndrome (SARS), COVID-19, or chronic obstructive pulmonary disease (COPD)).

The compliance of the bronchi is produced via the modulation of the Autonomic Pulmonary Pathway. In particular, the novel treatment presented herein stimulates the ABVN and/or the auriculotemporal nerve (ATN) which have projections to the NTS. The NTS projects to LC, PAG and RN (e.g., NRM). These brainstem nuclei deliver an inhibitory signal to airway-related pre-ganglionic neurons located in the nucleus ambiguus (NA). The NA sends a signal to the airway smooth muscle, via efferent pathways mainly through the vagus nerve, eliciting bronchodilation.

The anti-inflammatory effect is provided via activation of the Anti-inflammatory Pathway (a.k.a. the cholinergic anti-inflammatory pathway). In particular, the novel treatment described herein stimulates the ABVN and/or the ATN which, as stated before, have projections to the NTS; these projections elicit cholinergic anti-inflammatory effects via efferent pathways; mostly via the vagus nerve. A systemic anti-inflammatory response can be used to treat and/or prevent sepsis, which is one of the most expensive and highly deadly conditions. Another inflammatory condition which can be treated via a systemic anti-inflammatory response is pancreatitis. Pancreatitis is an acute or chronic inflammation of the pancreas, which can be caused by a variety of factors. Systemic anti-inflammatory effects occur when the vagus nerve mediates spleen function, thereby reducing the amount of circulating pro-inflammatory cytokines. In addition, a local anti-inflammatory effect occurs at organs reached by the efferent pathways; for example at the lungs, gut, and heart. In addition, modulation of spleen activity modifies platelets such that coagulation occurs faster and can also occurred in the presence of coagulation disorders such as hemophilia A, B and C as well as in other coagulation factor deficiencies, such as in Factor I, Factor II, Factor V, Factor VII, Factor X, Factor XII, and Factor XIII deficiency; furthermore, this is also the case in the presence of other clotting disorders such as for example in VWD.

For the above reasons and more, rapid production of effective and low cost transdermal neurostimulation devices can lead to great medical benefit across a wide swath of the population. The inventors recognized a need to develop new manufacturing techniques and stimulation delivery mechanisms to increase usability and therefore therapy compliance and to reduce manufacturing costs and increase manufacturing output, thereby enabling wider access to symptom relief and/or medical condition improvement for patients expressing the various disorders detailed above as well as additional disorders and conditions for which transdermal neurostimulation therapy may provide benefit.

SUMMARY OF ILLUSTRATIVE EMBODIMENTS

The inventors recognized a need to pursue seamless integration of the medical device with the desired form-factor of the wearable. The inventors achieved this integration by using the flexible wearable body of the wearable medical device as the substrate of a Printed Circuit (PC), achieving a three-dimensional (3D) circuit integrating the electronic components of the electrical auricular neuromodulator onto the geometry of the wearable. This offers many advantages over commonly used methods of integrating electronics and mechanical components. In the commonly used method, a rigid, flexible, or rigid-flex printed circuit board (PCB) is miniaturized as much as possible and then inserted into a housing which could be the wearable device itself. Interconnections between the PCB and the wearable are one of the most common failure points and thus, they are usually made very robust, thereby increasing cost, weight, and size. Additionally, user interfaces such as, for example, buttons or LEDs typically need to be close to or flush with the outer facing surface of the wearable. This is usually achieved by using extra components such as light-pipes and connecting rods that go from the circuit to the surface. In many cases, even with the use of such connecting components, the layout of the PCB is dictated by the desired location of the user interfacing components which is determined by the wearable, which seldomly aligns with what the best locations of such components would be in the PCB. For this reason, the location of the user interfacing components imposes restrictions on the PCB layout. Additionally, nowadays, the user interfacing components are usually the largest components on the circuit, which greatly limits the miniaturization of the PCB. Furthermore, even with the use of flexible or rigid-flex PCBs the circuit can be bent, but it cannot be stretched. Each of the above-noted limitations can be eliminated by the embodiments described herein.

In one aspect, the present disclosure relates to design and manufacturing techniques for creating a wearable auricular neurostimulator (WANS) having an integrated three-dimensional (3D) electronic circuit of electronic components including at least two electrode components for delivering neurostimulation. The WANS may include at least one earpiece assembly portion produced using a flexible and/or stretchable material (e.g., plastic, rubber, silicone, polyethylene terephthalate (PET), thermoplastic polyurethane (TPU), non-woven polypropylene, etc.). The earpiece assembly portion, for example, may be molded or three-dimensionally printed. One of the earpiece assembly portions has, built into its surface regions, the desired topography to place each of the electronic components of the three-dimensional circuit at a horizontal and/or vertical position best suited for that electronic component. For example, a button component may be provided a topographical footprint disposed close to one of the surfaces of the molded part. Traces between the electronic components may be printed using a conductive ink that allows for flexing and stretching of the substrate on which they are printed, thereby connecting the electronic components mounted at their various topographical surface locations into the electronic circuit. In some implementations, a layer of dielectric is deposited over all traces and/or electronic components. In some implementations, a second earpiece assembly portion is provided as a cover to seal the earpiece assembly of the WANS. The cover may be molded or three-dimensionally printed, for example, using one or more flexible materials. In some embodiments, a more traditional PCB (e.g., a rigid-flex PCB) may be combined with the printed 3D structure circuit to provide some advantages such as manufacturing advantages.

In some embodiments, the WANS is configured to be powered by a primary cell battery, such as a coin cell. Using a primary cell battery may be preferable when designing a fully disposable WANS.

In some embodiments, the WANS has a rechargeable battery. The battery, for example, may be designed for recharging via electromagnetic induction. In another example, the rechargeable battery may be recharged via a temporarily connected cable.

In some embodiments, the WANS is fully sealed to prevent water and dust ingress. The outer cover, for example, may provide a waterproof or water-resistant surface seal.

In one aspect, the present disclosure relates to a self-contained auricular electro-neuromodulator configured to be placed around the ear of a wearer such that surface electrodes are disposed in positions for electrically stimulating one or more branches of the vagus nerve and/or the trigeminal nerve to provide therapy to the wearer.

In some embodiments, the auricular electro-neuromodulator is configured to be placed around the ear of the wearer with at least one of its electrode components (e.g., at least one vagal-stimulating electrode) in close proximity to branches of the vagus nerve. In an example, the at least one vagal-stimulating electrode may be disposed in a position for stimulating the auricular branch of the vagus nerve (ABVN). The ABVN may be targeted, for example, by locating one or more of the vagal-stimulating electrodes for contact with the tragus of the wearer's ear. In another example, one or more of the vagal-stimulating electrodes may be located for contact with the cymba concha of the wearer's ear. In a further example, one or more of the vagal-stimulating electrodes may be located for contact with a section of skin behind the wearer's ear (e.g., the auricle skin, the head skin, or both), where it is in close proximity to the mastoid canaliculus (i.e., Arnold's canal), through which the ABVN surfaces from the temporal bone. In an additional example, the ABVN may be targeted by placing one or more of the vagal-stimulating electrodes for contact with the posterior surface of the ear canal of the wearer's ear. Since the ABVN has a branch connected to the posterior auricular nerve, in yet another example, the ABVN can be activated indirectly by stimulating the posterior auricular nerve. In this example, one or more of the vagal-stimulating electrodes can be positioned in a location for contact with skin behind the ear and/or the head skin positioned in close proximity to the posterior auricular nerve path.

In some embodiments, the auricular electro-neuromodulator is configured to be placed around the ear of the wearer with at least one of its electrode components (e.g., a trigeminal-stimulating electrode) in close proximity to branches of the auriculotemporal nerve (ATN). The ATN may be targeted, in one example, by placing one or more of the trigeminal-stimulating electrodes on the facial skin of the patient in front of the ear. In illustration, the facial skin may be positioned to cover or be in close proximity to the temporomandibular joint. In another example, the ATN may be targeted by placing one or more of the trigeminal-stimulating electrodes for contact with the anterior part of the wearer's ear canal though which a branch of the ATN (e.g., the nervus meatus acustici externi) travels.

In some embodiments, the auricular electro-neuromodulator is configured to be placed around the ear of the wearer with at least one of its electrode components (e.g., an ABVN-stimulating electrode) in close proximity to a position at which the ABVN surfaces via the MsC. Using different approaches, a number of researchers have targeted the ABVN via the ear canal as well as the cymba conchae and the interior tragus. However, modulating ABVN activity (directly or indirectly) as it surfaces through the MsC is a novel concept which provides great usability and manufacturability advantages.

The foregoing general description of the illustrative implementations and the following detailed description thereof are merely exemplary aspects of the teachings of this disclosure and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings.

DETAILED DESCRIPTION OF ILLUSTRATIVE EMBODIMENTS

Figure 1:
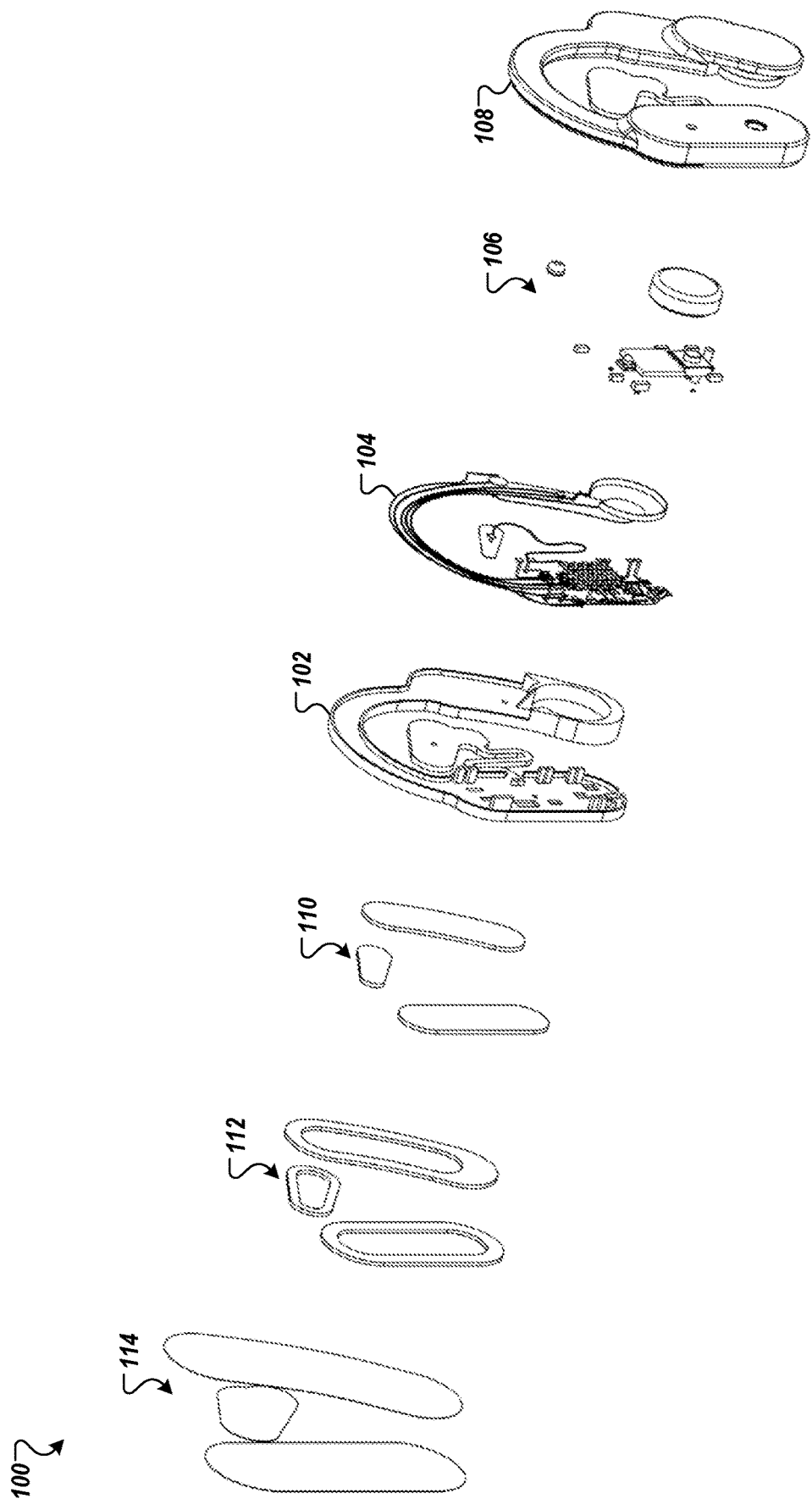
FIG. 1 is a block diagram of an exploded view of components of an example wearable auricular neurostimulator (WANS) apparatus.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

FIG. 1 is a block diagram of an exploded view of components of an example wearable auricular neurostimulator (WANS) apparatus 100 with integrated three-dimensional printed circuitry for advantageously positioning circuitry components in a compact and convenient arrangement. The WANS apparatus 100, as illustrated, includes a body 102, printed circuitry 104 for depositing on the body 102, a set of electronic components 106 for adding to the printed circuitry 104 at printed connection points, a cover 108 for enclosing the printed circuitry 104 and electronic components 106 in the body 102, a conductive adhesive (e.g., hydrogel or a dry material such as FLEXcon® OMNI-WAVE™ by FLEXcon Company, Inc. of Spencer, MA) 110 configured to transfer energy from the WANS apparatus 100 to the skin of a wearer, a non-conductive adhesive (e.g., hydrocolloid, or a dry skin adhesive) 112 to increase adhesion between the WANS apparatus 100 and the skin of the wearer, and one or more liners 114 for protecting the adhesive elements prior to wearing.

In some implementations, the body 102 is a flexible and/or stretchable wearable substrate designed to comfortably form to the contours of the wear of the wearer. The body 102, for example, may be formed using rubber, plastic (e.g., PET, TPU, non-woven polypropylene, etc.), and/or silicone. In some examples, the body 102 may be three-dimensionally printed and/or molded. The body 102, for example, may be formed as a contiguous molded piece of a single material. In another example, the body 102 may be formed of two or more materials, for example in a layered or two-step process. As illustrated, the body 102 includes multiple surface wells and protrusions for enabling printing and/or positioning of the circuitry 104 along a three-dimensional surface.

Figure 2A:
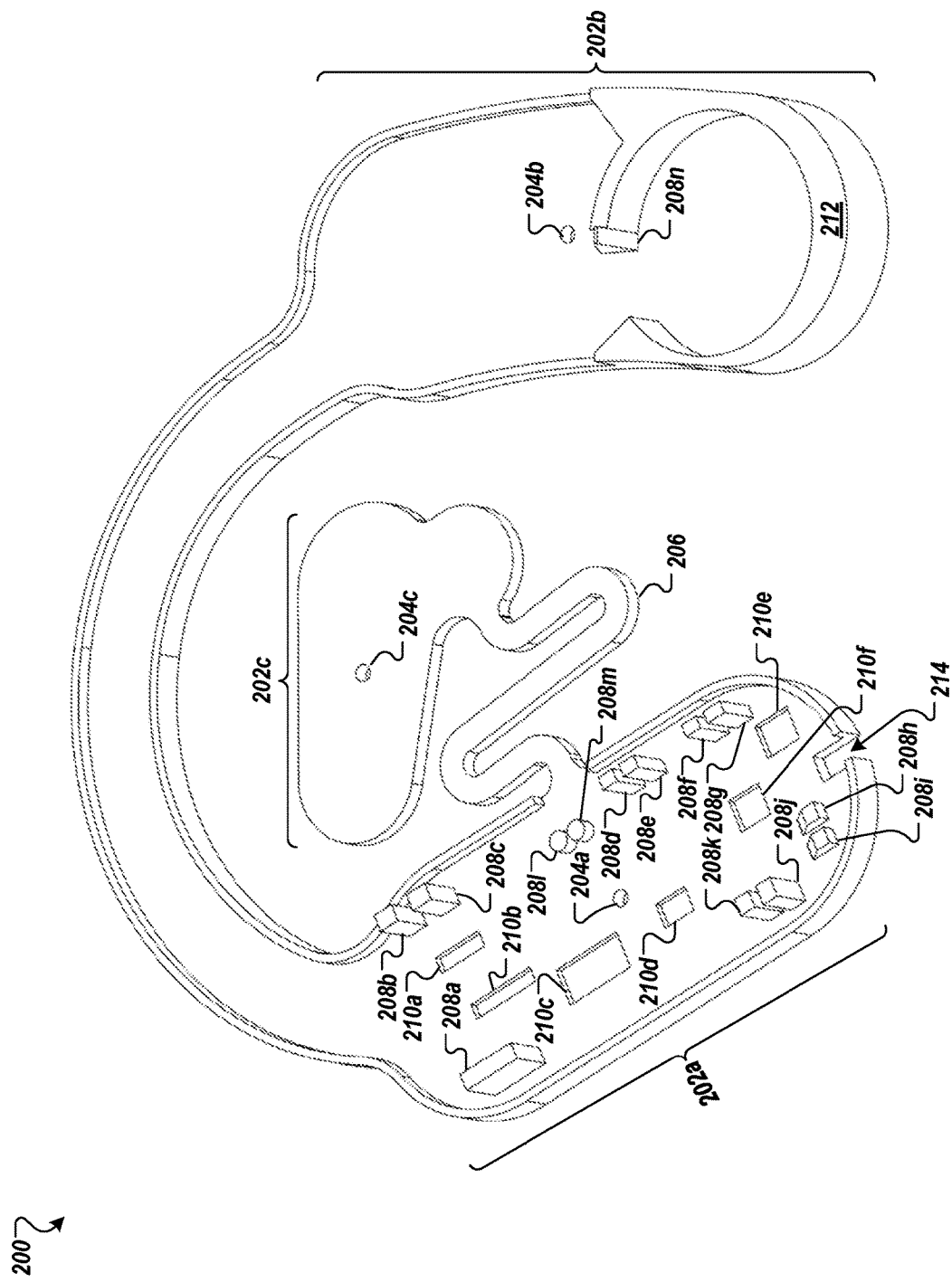
FIG. 2A through FIG. 2G illustrate example three-dimensional topography, printed circuitry, and added electronic devices for forming various components of example WANS apparatuses.

Turning to FIG. 2A, a first example WANS wearable body section 200 can be viewed as including a forward portion 202a, a rear portion 202b, and an on-ear portion 202c, each portion including at least one opening 204a-c for an electrode. When donned by a wearer, the WANS may be wrapped around the ear such that forward portion 202a is disposed in front of the ear and the rear portion 202b is disposed behind the ear. The on-ear portion 202c, connected to the forward portion 202a by a flexible connector 206, may be frictionally and/or adhesively retained in a cymba region of the ear. The on-ear portion 202c, in some embodiments, is formed of a different material than the forward portion 202a and rear portion 202b. For example, the on-ear portion 202c may be designed to exhibit different characteristics than the forward portion 202a and rear portion 202b such as, in some examples, deformability, adherence, and/or differing levels of flexibility.

In some implementations, one or more protrusions are developed into the material of the wearable body section 200. For example, the forward portion 202a includes a set of protrusions 208a-m. In another example, the rear portion 202b includes a protrusion 208n as well as a rounded wall feature 212. Although the majority of the protrusions 208 are generally rectangular or circular in shape, in other embodiments, protrusions may be formed of a variety of geometries. Certain protrusions, in some examples, may be provided to mount or locate certain circuitry elements, such as, in some examples, LEDs, control buttons, and/or sensors, closer to the outer surface of the WANS device. For example, while treatment electrodes are deposited on the skin-facing surface of the WANS, for convenience of use, any control buttons may be positioned near a more accessible surface of the WANS. Some protrusions 208, for example, may be formed as landing zones for pick and place circuitry components. Some protrusions 208 may be formed in part to support separation of the body section 200 from a corresponding cover or other body section, for example to protect circuitry components from being crushed during use. At least some protrusions 208, for example protrusions 208h and 208i, may be formed with angled sides such that if circuitry traces are deposited or flexible circuit traces go up the protrusions 208h and 208i then they do not form a 90 degree angle. The angle (e.g., up to 80°, up to 70°, about 45°, etc.) may be selected for depositing smooth electrical traces and/or to enhance durability of traces (e.g., deposited electrical traces and/or flexible circuitry traces). Different protrusions 208 may be developed using different materials and/or printing compositions to enhance properties of the protrusions. For example, certain protrusions 208 may be designed to be substantially flexible (e.g., the same or similar to the flexibility of the body section 200), while other protrusions 208 may include stiffening materials or components to enhance rigidity. In some examples, protrusions designed to support a heavier electronic component and/or to maintain separation between the body section 200 and a second body section or cover may be printed to incorporate enhanced rigidity. Protrusions, in certain examples, may be deposited with an aspect ratio designed to support the electronic component at the desired height while substantially maintaining the position of the electronic component and/or without incurring breakage due to stress upon the protrusion.

One or more wells, in some implementations, are developed into the material of the wearable body section 200. The forward portion 202a, for example, includes a set of wells 210a-f. Certain wells 210, for example, may provide a positioning for electrical components, such as, in some examples, capacitors, sensor components, power components, processing circuitry components, memory components, and/or functional sub-units such as flex, flex rigidized, or rigid-flex circuits, that require additional vertical space between the body section and the corresponding cover or other body section. In another example, some wells 210 may provide for snug and/or precision positioning of electrical components. Further, at least a portion of the wells 210 may provide positioning proximate a region of interest. For example, wells 210 may be created for positioning a temperature sensor, acoustic sensor, an electrocardiogram (ECG) sensor, and/or vibrational sensor proximate the skin to better collect biometric data. In an additional example, at least a portion of the wells 210 may provide a collection region for placing an adhesive used to secure a larger electronic component to the wearable body section 200. The electronic component, for example, may be placed onto the adhesive region prior to printing the three-dimensional circuitry traces.

In some implementations, the wearable body section 200 includes one or more port regions for connecting to the circuitry within the WANS. For example, the wearable body section 200 includes a port 214 provided to electrically connect external circuitry (e.g., a charging device, a controlling device, one or more tethered sensors, etc.) to the WANS. In other implementations, the port 214 is provided for use as a routing channel for wrapping the 3D printed circuitry to other areas of the WANS, such as an external position.

Returning to FIG. 1, the printed circuitry 104 for depositing on the body 102, in some implementations, is printed using a conductive ink that allows for flexing and stretching of the substrate on which the circuitry traces are printed, thereby connecting the electronic components 106 mounted at their various topographical surface locations of the body 102 into the printed circuitry 104. The printed circuitry 104, in some examples, may include connecting traces, logic components, electrodes, and/or conductive pads for receiving electronic components. In some cases, the electronic components may include a populated rigid-flex circuit.

Figure 2D:
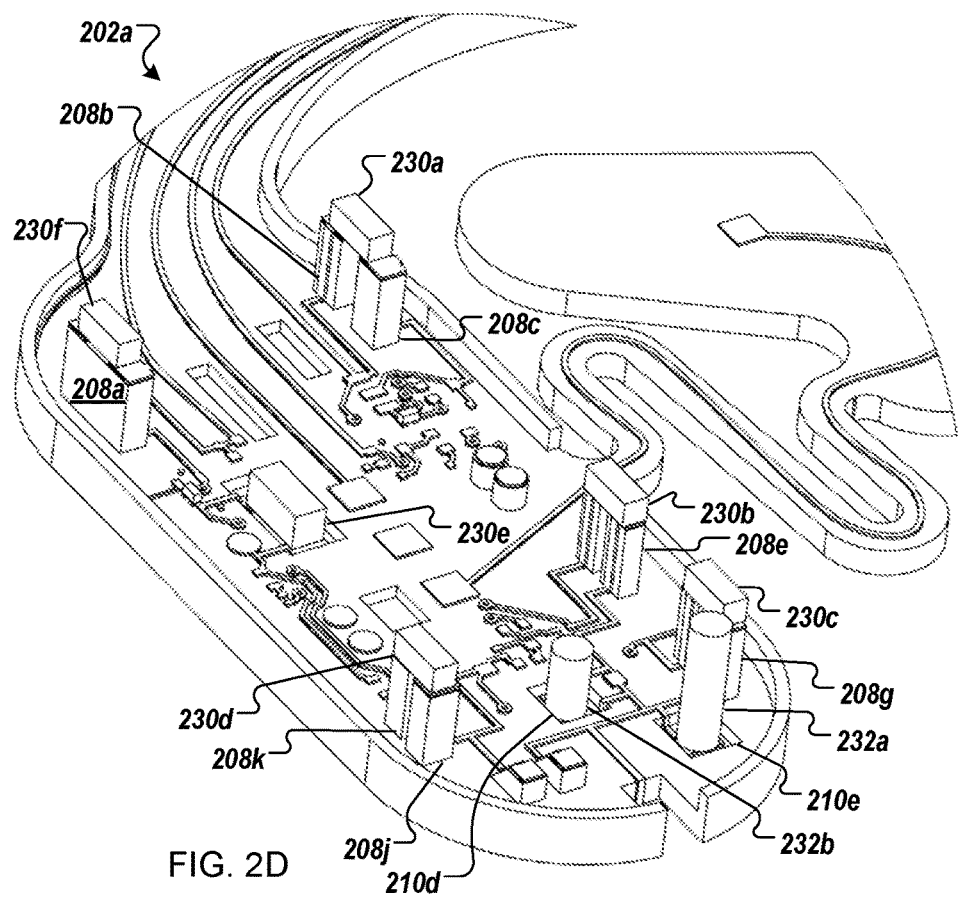
Figure 3:
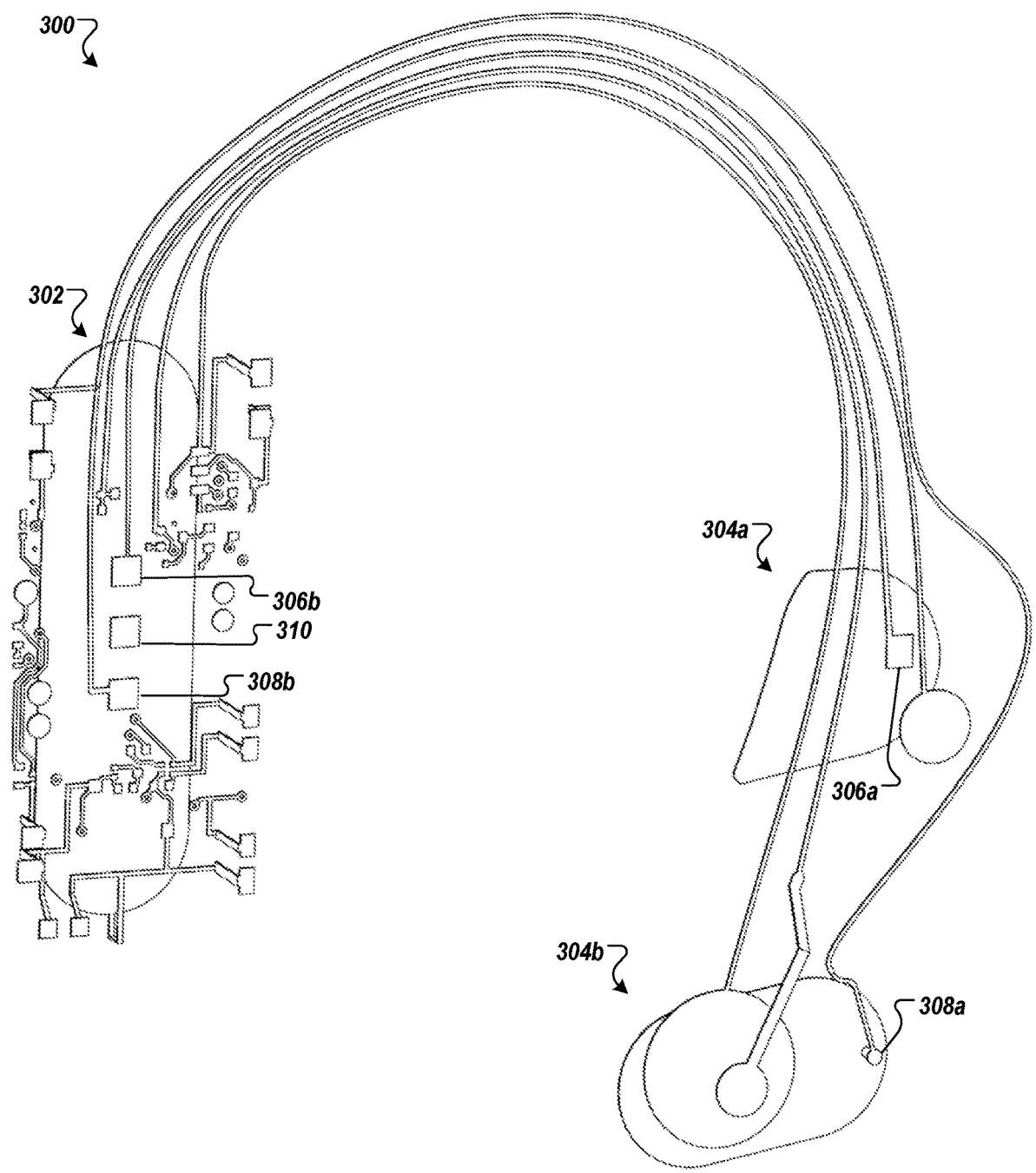
FIG. 3 illustrates example three dimensionally printed flexible circuitry for a WANS apparatus.

FIG. 3 illustrates an example layout of printed circuitry 300 for another WANS apparatus. Turning to FIG. 3, the printed circuitry 300 includes a forward portion 302 (e.g., similar to a layout of the printed circuitry of the forward portion 202a illustrated in FIG. 2D), an upper rear portion 304a, and a lower rear portion 304b. The upper rear portion 304a includes an electrode 306a connected to pairing 306b on the forward portion 302. The lower rear portion 304b includes an electrode 308a connected to pairing 308b on the forward portion 302. The forward portion 302 additional includes an electrode 310.

Figure 2B:
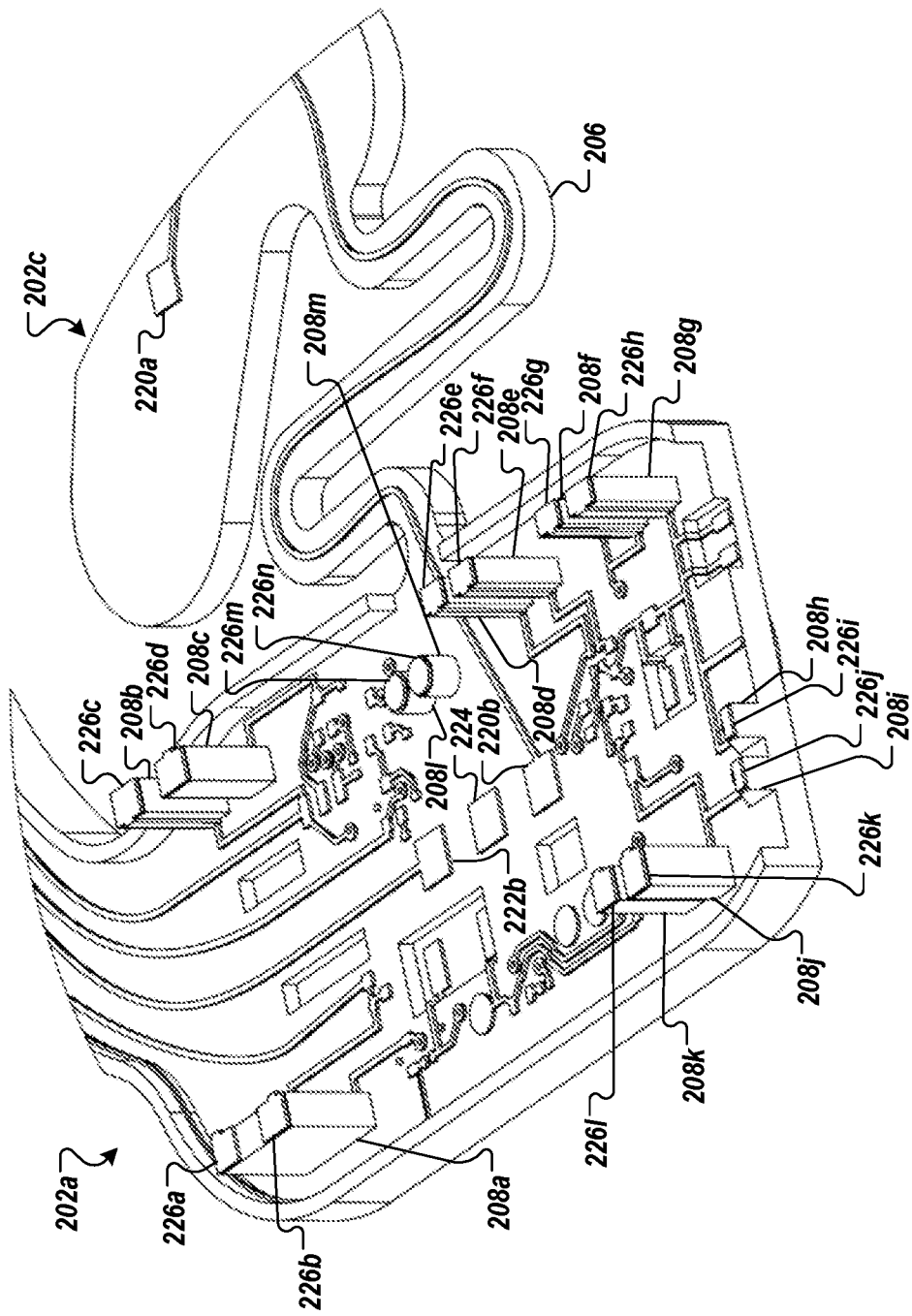

Turning to FIG. 2B, a partial view of the wearable body section 200 of FIG. 2A illustrates printed circuitry deposited upon the forward portion 202a and the in-ear portion 202c. As shown, electrical traces are defined up each protrusion 208a-m to an electrical contact deposited thereon (e.g., electrical contacts 226a-n). Further, the same partial view of the wearable body section 200 is replicated in FIG. 2C, this time including labels referencing the wells 210a-e. As illustrated well 210c includes two electrical contacts 228a, 228b deposited therein. Similarly, well 210e has two electrical contacts 228c, 228d deposited therein, and well 210f has two electrical contacts 228e, 228f deposited therein.

Figure 2C:
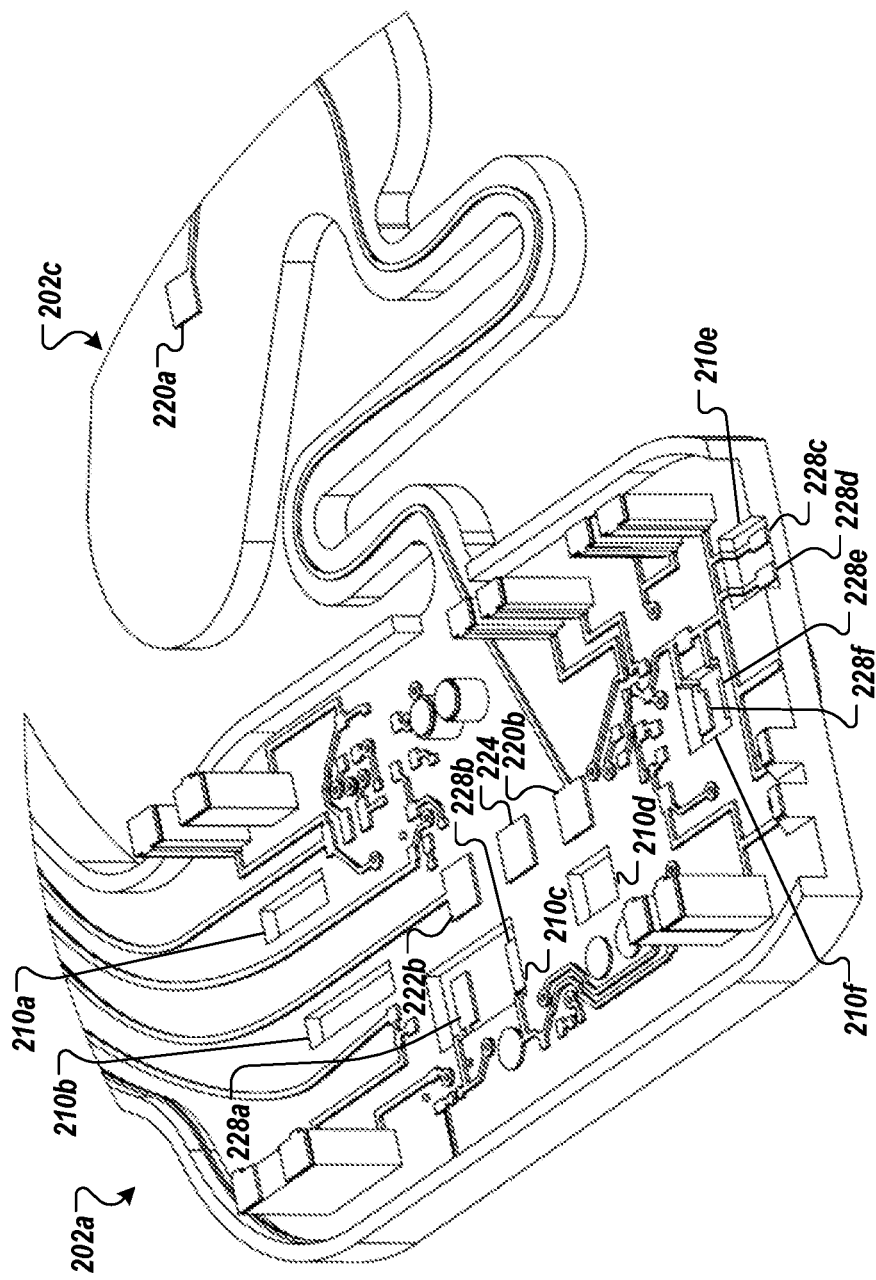

As illustrated in FIG. 2B and FIG. 2C, a first electrode pairing 220a, 220b is deposited between the in-ear portion 202c (e.g., deposited over the opening 204c of FIG. 2A) and the forward portion 202a. An electrode pad 222b of a second electrode pairing (e.g., between the forward portion 202a and the rear portion 202b) is positioned at an opposite side of a forward portion electrode 224 (e.g., deposited over the opening 204a of FIG. 2A). The electrode pairings, for example, may be positioned for contact with driving circuitry for delivering therapeutic pulses via the electrodes (e.g., 220a and 224).

Although illustrated as a single layer of printed circuitry, in other embodiments, multiple layers may be developed, for example by depositing additional flexible material of the wearable body section 200 on top of at least a portion of the first layer of printed circuitry and/or a layer of dielectric material. In further embodiments, a second layer of circuitry may be deposited in a corresponding wearable body section 200 (e.g., similar to the cover 108 of FIG. 1), and the layers of circuitry may be connected when pressing the first body section and the second body section together.

Returning to FIG. 1, in some implementations, various electronic components 106 are added to the printed circuitry 104. The electronic components 106, in a first example, may include motion sensor components such as, in some examples, one or more accelerometers and/or gyroscopes (e.g., a MEMS gyroscope) for tracking movement and/or orientation of the wearer. In illustration, a gyroscope may be used to determine when a wearer is not in a generally vertical orientation, such as a disoriented pilot who may not be aiming along the horizon, to apply stimulations for treating motion sickness. Similarly, an accelerometer may be used to determine when a pilot's body is being exposed to G-forces that could lead to motion sickness. In other illustrative examples, a motion sensor may be used to recognize involuntary movements of a wearer, such as physical tics/tremors, or to track activity of the wearer (e.g., an exercise routine). In a second example, the electronic components 106 may include one or more off-the-shelf biometric monitoring electrical sensors, vibrational sensors, and/or acoustic sensors to recognize biometric signatures of the wearer (e.g., pulse, heart rate, etc.). The biometric signatures, for example, may be used as feedback to control therapy (e.g., begin, adjust, and/or end). In a third example, the electronic components 106 may include a power source, such as a battery. The electronic components 106, in a fourth example, may include input/output (I/O) devices such as, in some examples, one or more buttons, one or more switches, one or more pressure touch sensors, one or more light emitting diodes (LEDs), one or more speakers, one or more microphones, and/or one or more connectors (e.g., a cable connector or multi-pin connector) for tethering an external device. The external device, in illustration, may be a controller such as a stimulation generator and/or an external power source.

In some implementations, the electronic components 106 include one or more integrated circuits (ICs) and/or printed circuit boards (PCBs). PCBs may be used, in some example, to add a boost converter to control impedances at critical locations in the circuitry. A PCB, in another example, may include a quad flat no-lead (QFN) package for heat dissipation. A Bluetooth IC module or other wireless transceiver, in another example, may be added to provide wireless communications between the WANS apparatus 100 and a controller and/or separate WANS device, such as WANS devices designed as a pair to coordinate therapy delivered to both the right and left ears of the wearer.

In some embodiments, wireless communication enables the WANS to communicate with a sensor. In some cases, the sensor can provide a feedback signal to adjust or control the therapy provided by the WANS. For example, a biosensor assessing the concentration of cortisol in the skin can provide a signal to determine the level of stress of the user. In another case, the sensor may be used to assess electromyography (EMG) activity and provide early detection of the intent to activate a muscle or a motion sensor may provide information about the movement of a limb. In these two cases, the sensor signal could be used as a trigger for a stroke recovery training protocol, for example. In yet another example, a sensor providing pupillometry measurements can be used as a measure of attention, alertness, or wakefulness (or the lack thereof). Such a signal could be used as feedback to adjust therapy to maintain a desired level of attention, alertness, and/or wakefulness. Similarly, in a further example, attention, alertness, and/or wakefulness can be assessed by an ultrasonic sensor measuring cerebral blood flow velocity (CBFV). In such an example, CBFV can be used as feedback to adjust therapy.

In some implementations, robotic pick and place manufacturing is used to add at least a portion of the electronic components 106 to the printed circuitry 104. The robotic system, for example, may use coordinate placements programmed based on the printing coordinates to align the electronic components 106 with contact pads printed for each electronic component 106. In another example, an automated system may use sensors to detect the printed contact pad coordinates for adding various electronic components 106.

In some implementations, at least a portion of the electronic components 106 are soldered into position. For example, manual or robotic soldering may be performed to connect certain electronic components 106. At least a portion of the electronic components 106, in some implementations, are attached to the printed circuitry 104 using a conductive epoxy. In further implementations, at least a portion of the electronic components 106 are fitted into position using pins, snaps, or other mechanical connectors to permanently or releasably fix each electronic component 106 into position on the printed circuitry 104. In some implementations, heat and/or ultraviolet (UV) curing provides sufficient attachment of certain electronic components 106 to the printed circuitry 104, such as printed pads.

Turning to FIG. 2D, in a first addition of electronic components to the forward portion 202a, a set of electronic components 230a-f have been mounted to protrusions 208a-k. Further, electronic components 232a and 232b have been added to wells 210d and 210e.

Figure 2E:
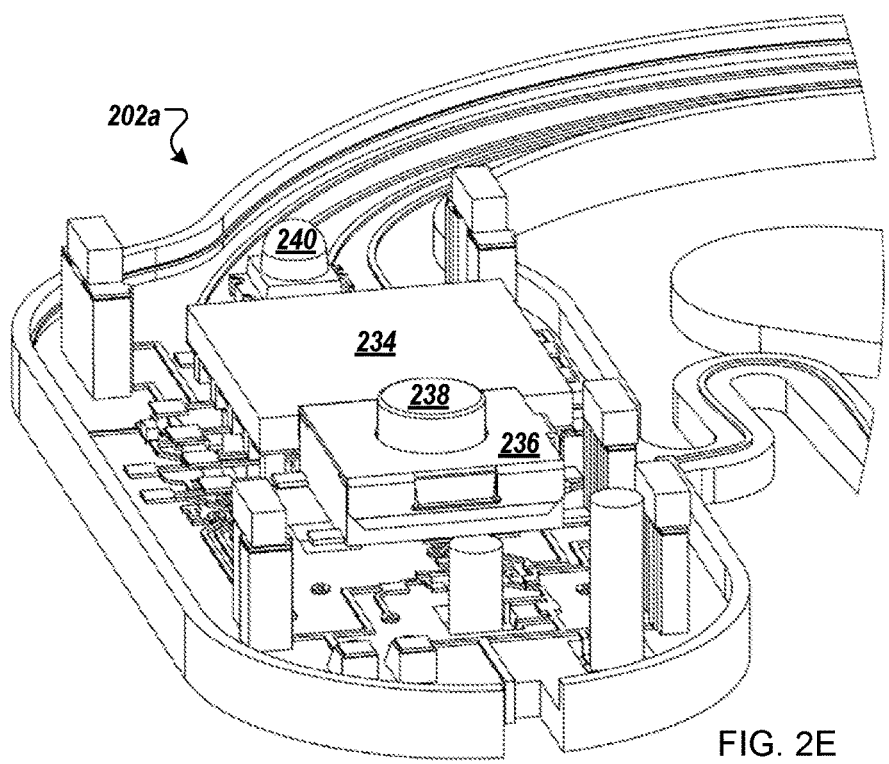

Turning to FIG. 2E, in a second addition of electronic components to the forward portion 202a, a PCB or IC 234, an input control 236 with press button 238, and an LED 240 have been added to a region including the wells 210a, 210b, and 210d, the electrode 224, the electrode pairings 222 and 220b.

Figure 2F:
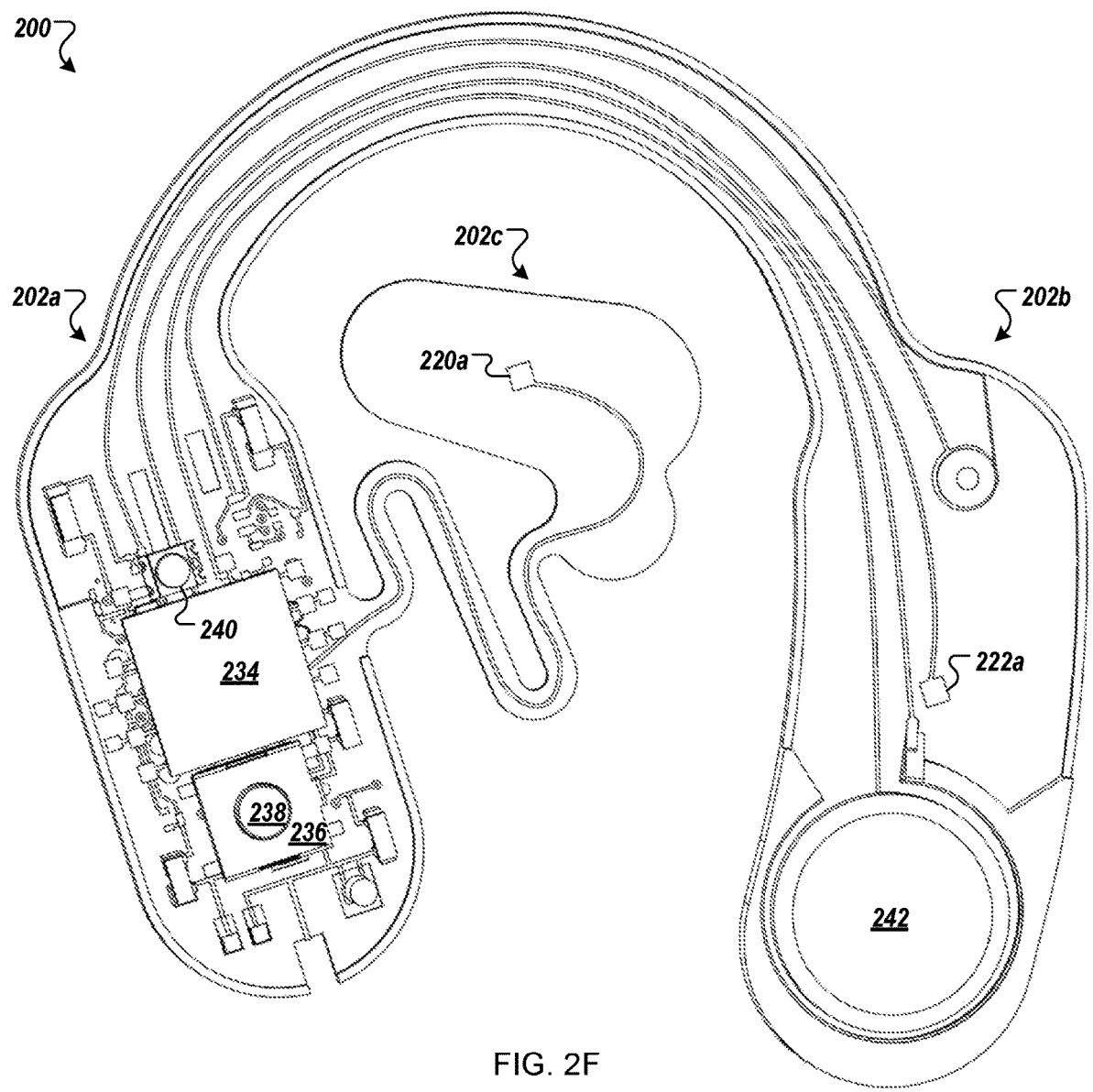
Figure 2G:
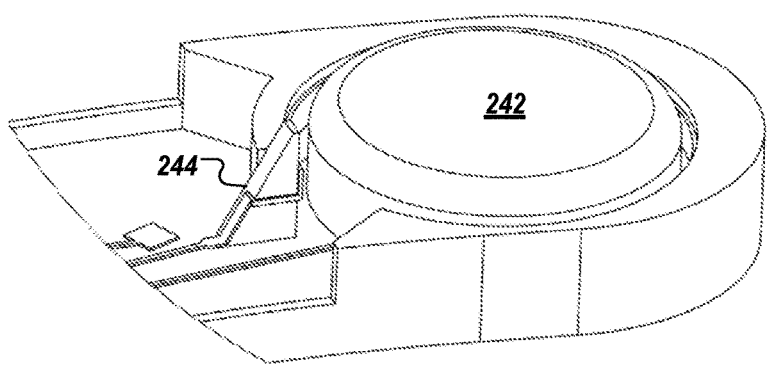

In FIG. 2F, an overhead view of the WANS wearable body section 200 illustrates the completed circuitry including the positioning of additional electronic components. As illustrated, the rear portion 202b includes a power element 242 (e.g., button cell battery). To connect to the power element 242, as shown in FIG. 2B, a ramped protrusion 244 provides an angled surface for deposition of the printed circuitry trace, thereby avoiding a right-angle or similarly tight (e.g., over 85°, over 80°, over 75°, etc.) angle deposition which may be more prone to damage or breakage.

Figure 4:
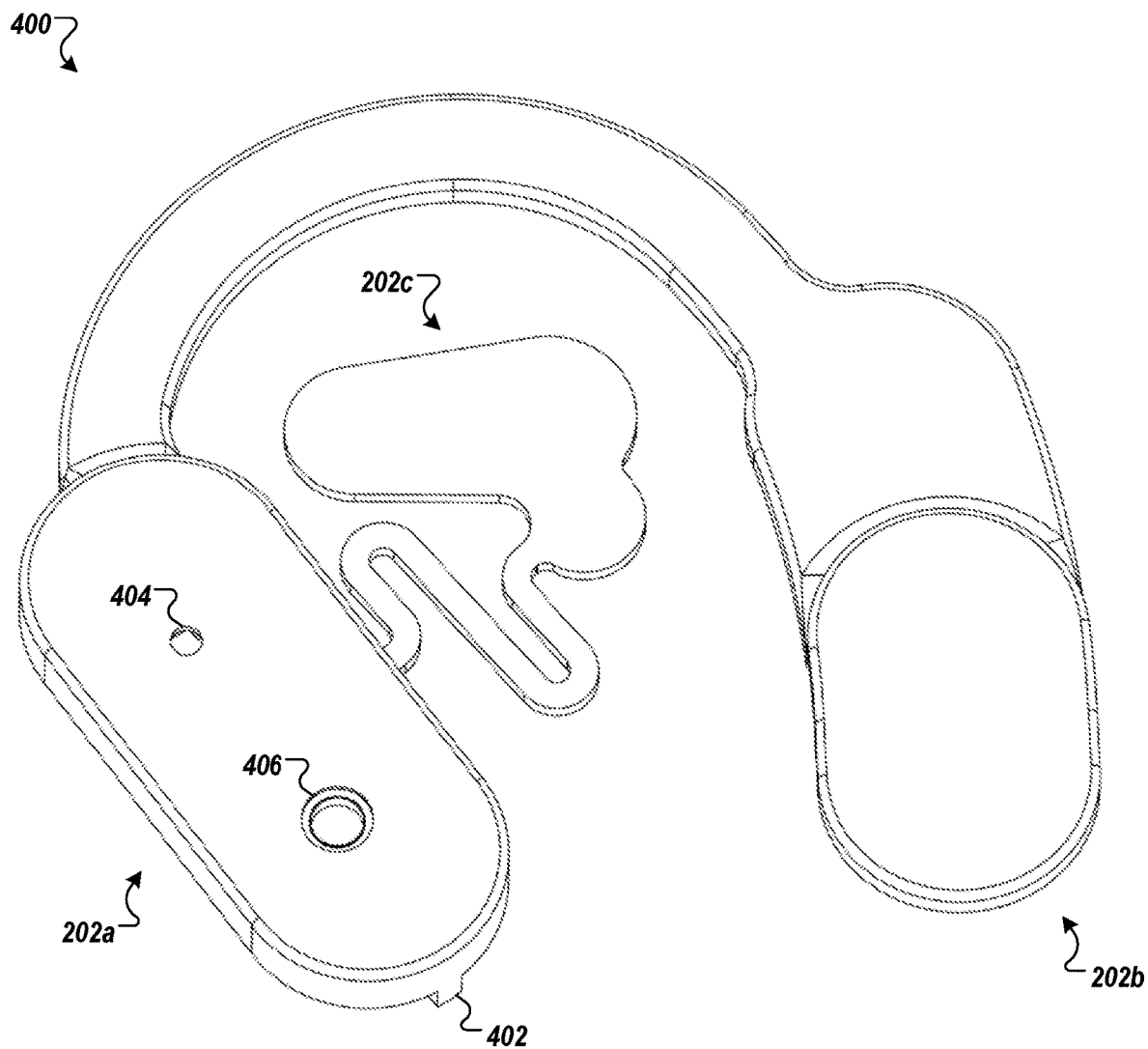
FIG. 4 illustrates an example cover for a WANS apparatus.

Returning to FIG. 1, in some implementations, after completing the circuitry deposition 104 and circuit component addition 106 in the body section 102, the cover 108 may be added to enclose the printed circuitry 104 and electronic components 106 in the body 102. The cover 108, as illustrated, may be formed as a cap or lid that extends substantially down the sides of the body section 102. In other embodiments, the cover 108 may at least partially wrap around the body section 102, for example for increased water resistance and/or for increased retention. The cover 108 may be formed of a same material as the body section 102 or different material. For example, the cover 108 may be molded or three-dimensionally printed using one or more flexible materials. The cover 108, in some embodiments, is overmolded onto the body section 102. An overmolded cover 108 may be formed using one or more flexible materials which are the same or different than the material of the body section 102. The cover 108 may include one or more openings for passage of I/O electrical components, such as, in some examples, one or more buttons, a power cord connector, a controller connector, and/or an LED. The cover may further include openings to enable skin contact with one or more electrodes. In some embodiments, the cover 108 includes one or more transparent regions, for example to allow a visual indicator such as an LED to shine through. Turning to FIG. 4, for example, a cover 400 for the body section 200 of FIG. 2A through FIG. 2G includes a connector port 402, an LED port 404, and a button control port 406.

Returning to FIG. 1, in some implementations, the conductive adhesive 110 is added to a back side of the body section 102 of the WANS at the position(s) of the electrode(s) for transferring energy from the electrodes of the WANS apparatus 100 to the wearer's skin. The conductive adhesive 110, for example, may include a hydrogel and/or another conductive adhesive suitable for skin contact (e.g., a carbon based adhesive). Depending upon the position of the electrodes, in some embodiments, the conductive adhesive may be deposited on a front side of the cover 108 as well as the back side of the body section 102. In some embodiments, the conductive adhesive 110 is a conductive double-sided tape that is positioned manually or robotically over electrode positions on the WANS apparatus 100. The conductive adhesive 110, in some embodiments, is three-dimensionally printed onto sections of the WANS apparatus 100. In embodiments using directional conductive epoxy, the epoxy may be provided over a wider surface (e.g., across multiple electrodes or otherwise substantially coating skin-contacting surfaces of the WANS apparatus 100) due to the directional conductive epoxy being conductive in only the Z-direction when cured under a magnetic field.

Figure 5:
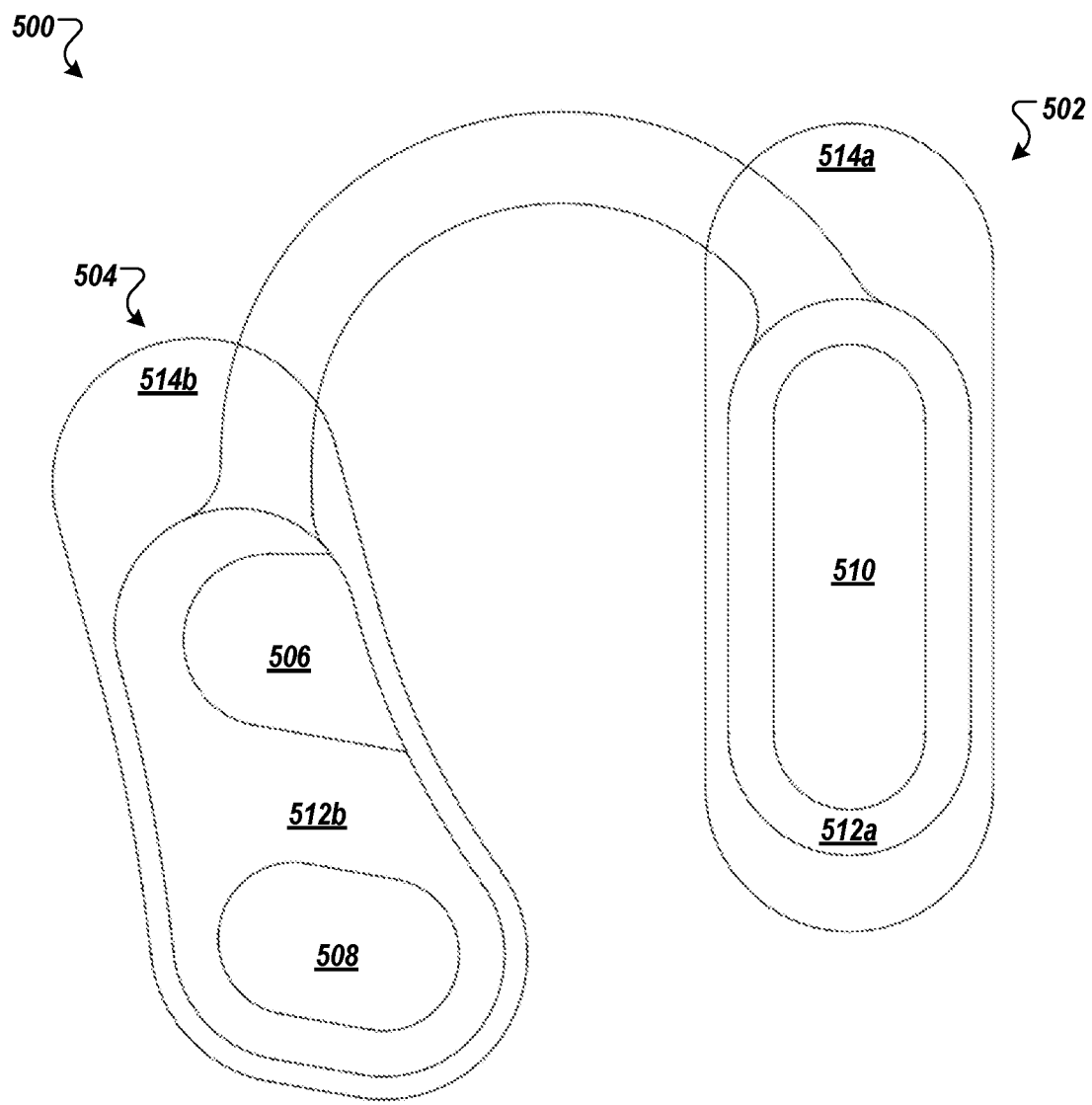
FIG. 5 illustrates example adhesive region layouts and protective liner positioning for an exterior skin-facing surface of a WANS apparatus.

Turning to FIG. 5, a WANS apparatus 500 includes a forward portion 502 including a conductive adhesive region 510 and a rear portion 504 including conductive adhesive regions 506 and 508. The conductive adhesive region 510 of the forward portion 502, for example, may correspond to the electrode 310 of the circuitry 300 of FIG. 3. Similarly, the conductive adhesive region 506 may correspond to electrode 306a of FIG. 3, and the conductive adhesive region 508 may correspond to the electrode 308a of FIG. 3.

Figure 8A:
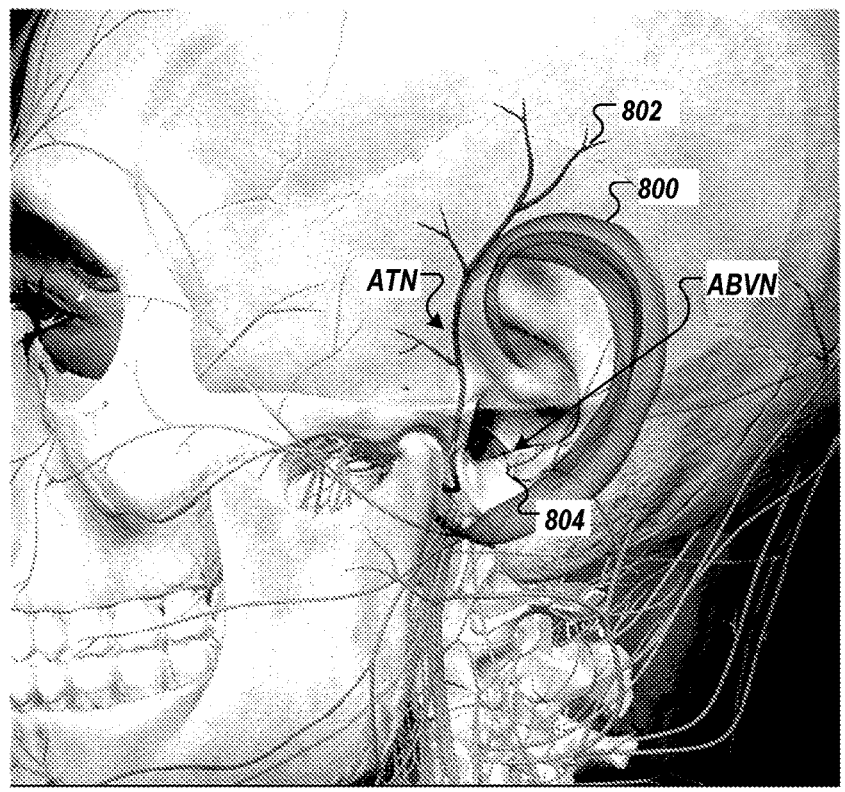
FIG. 8A through FIG. 8D, FIG. 9, and FIG. 10 illustrate example target nerve regions for directing therapy using a WANS apparatus.
Figure 8B:
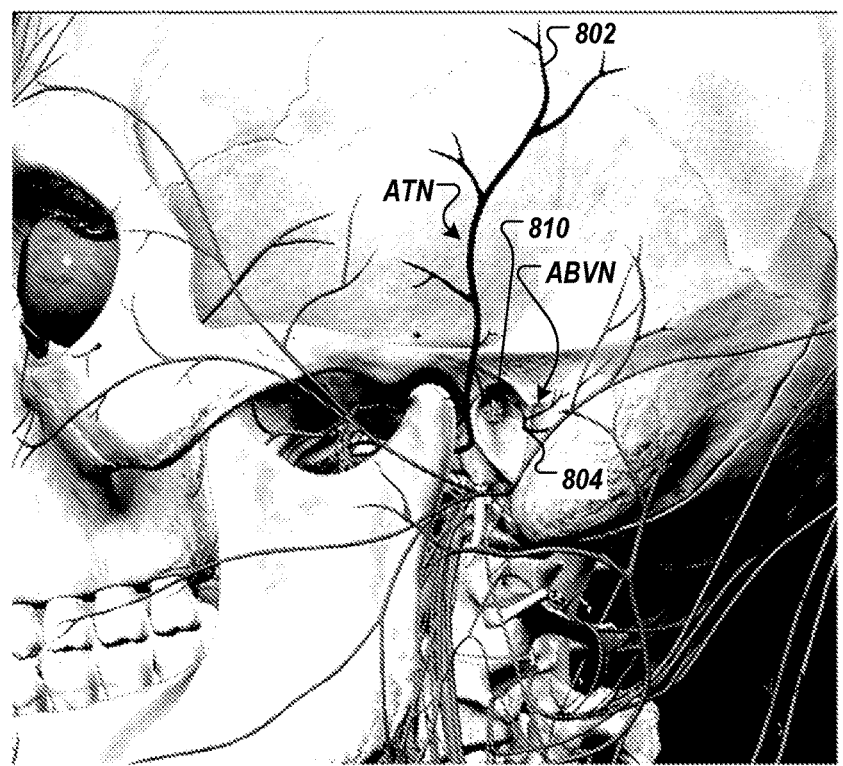

The conductive adhesive region 510, in some implementations, is configured to contact skin of a wearer in a region of nerve structures of the auriculotemporal electrode (ATN) and/or nerve structures connected to the ATN, such that delivery of therapeutic stimulation via the conductive adhesive region 510 modulates ATN activity. Turning to FIG. 8A and FIG. 8B, for example, ATN 802 is illustrated in relation to an ear 800 of a person (FIG. 8A), running generally in front of the ear 800, as well as in relation, skeletally (FIG. 8B), to an ear canal 810. In an illustrative example, an electrode in electrical communication with the conductive adhesive region 506 (e.g., the electrode 308a of FIG. 3) may be positioned in proximity to the temporomandibular joint.

Figure 8C:
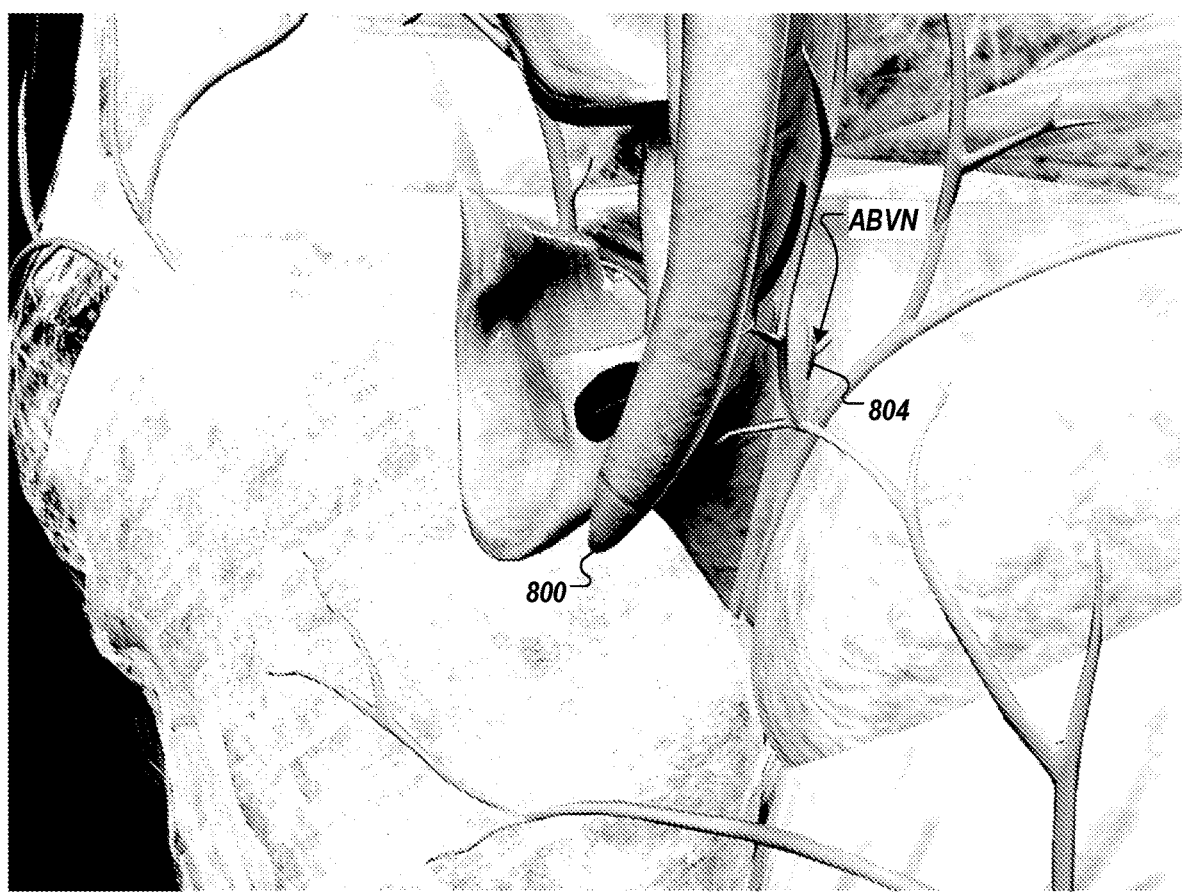
Figure 8D:
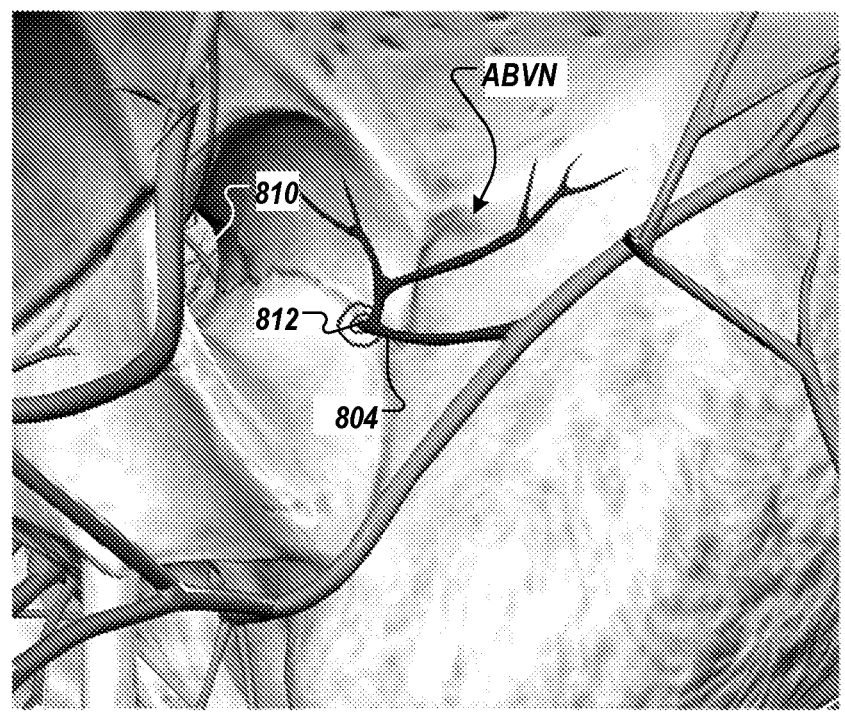
Figure 9:
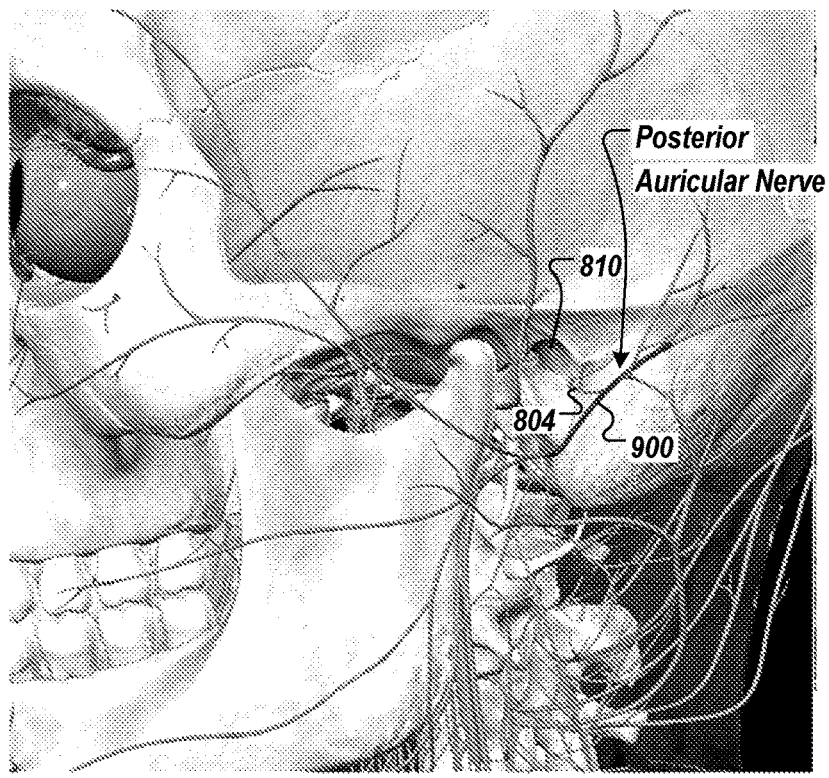

In some embodiments, the conductive adhesive region 506 is configured to contact skin of a wearer in a region of nerve structures of the auricular branch of the vagus nerve (ABVN) and/or nerve structure connected to the ABVN such that delivery of therapeutic stimulations via the conductive adhesive region 506 modulates ABVN activity. As shown in FIG. 8A through FIG. 8D for example, ABVN 804 is illustrated as it surfaces (FIG. 8D) through the mastoid canaliculus (MsC) 812 (e.g., Arnold's canal) and in relation to the ear 800 (FIG. 8A), in relation to the ear canal 810 (FIG. 8B) and in relation to the back of the ear (FIG. 8C). Turning to FIG. 9, posterior auricular nerve 900 meets a branch of the ABVN, providing another target for ABVN stimulation. In an illustrative example, an electrode in electrical communication with the conductive adhesive region 506 (e.g., the electrode 306a of FIG. 3) may be positioned in proximity to the MsC.

The conductive adhesive region 508, in some embodiments, is configured to contact skin of the patient as a return electrode, thereby forming an electrical circuit across the tissue with the electrodes corresponding to each of the forward conductive adhesive region 510 and the rear conductive adhesive region 506. Although illustrated as a single return electrode (e.g., region 508) for each positive electrode corresponding to adhesive region 510 and adhesive region 506, in other embodiments, separate return electrodes may be provided for each positive electrode. In further embodiments, three or more return electrode paths may be provided for the two positive electrodes. Other combinations are possible.

Figure 10:
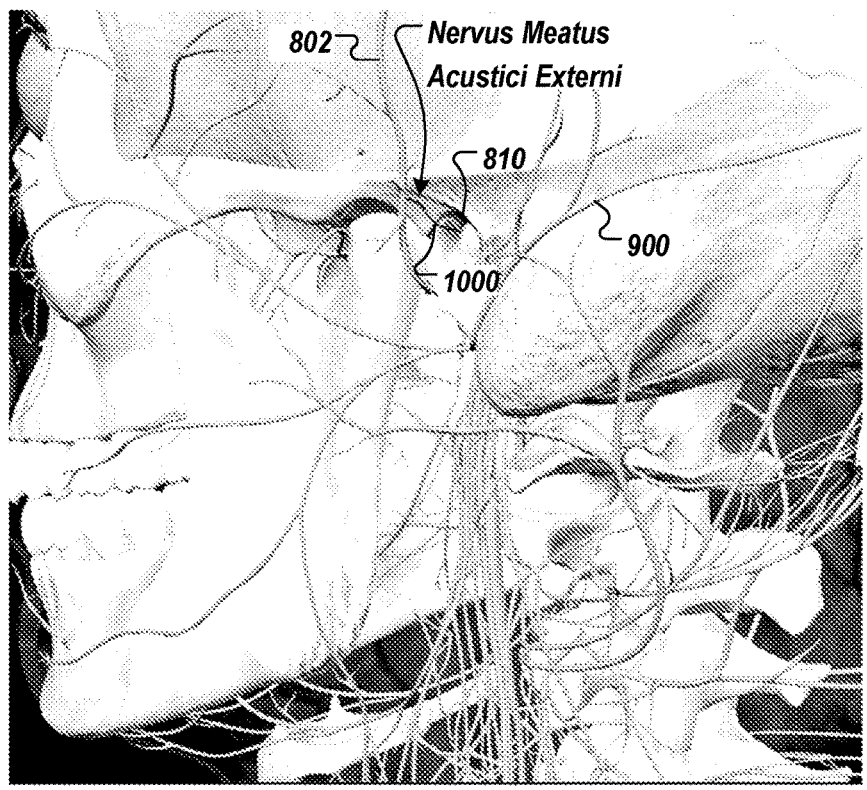

Turning to FIG. 2F, a conductive adhesive region may similarly be provided to create an electrical communication path from the electrode 220a of the wearable body section 200 to skin of the wearer in an anterior part of the ear canal. Turning to FIG. 10, the electrode 220a, for example, may be positioned to stimulate the nervus meatus acustici externi branch 1000 of the ATN 802.

Returning to FIG. 1, in some implementations, the non-conductive adhesive 112, such as a hydrocolloid, is applied to the WANS 100, generally surrounding each region of conductive adhesive 110. For example, as illustrated in FIG. 5, the non-conductive adhesive 112 may be provided generally in regions 512a (e.g., around conductive adhesive 510) and 512b (e.g., between conductive regions 506 and 508, around region 508, and at least partially around region 506). The non-conductive adhesive 112, for example, may be used to electrically isolate conductive regions created through electrical communication between electrodes and the conductive adhesive 110. In this manner, the non-conductive adhesive 112 may be used to avoid short-circuiting of the WANS apparatus 100. The non-conductive adhesive 112, in some examples, may be deposited (e.g., sprayed, three-dimensionally printed, etc.) on a front side of the cover 108 as well as the back side of the body section 102. In some embodiments, the non-conductive adhesive 112 is a double-sided tape that is positioned manually or robotically on the WANS apparatus 100. Rather than using a non-conductive adhesive, in other embodiments, a gripping material and/or pattern is molded into and/or three-dimensionally printed onto sections of the WANS apparatus 100. For example, three-dimensional adhesive microstructures may be provided on the surface of the body 102 and/or cover 108 to increase retention of the WANS apparatus about the wearer's ear.

In some implementations, one or more liners 114 are placed over the adhesive regions (e.g., conductive adhesive 110 and non-conductive adhesive 112) to maintain stickiness and cleanliness of the adhesive material prior to wearing. As illustrated in FIG. 5, for example, a forward liner 514a is illustrated as covering the adhesive regions 510 and 512a of the forward section 502, and a rear liner 514b is illustrated as covering the adhesive regions 506, 508, and 512b of the rear section 504. In other embodiments, a single liner may be provided to cover all adhesive regions of the WANS.

Figure 13A:
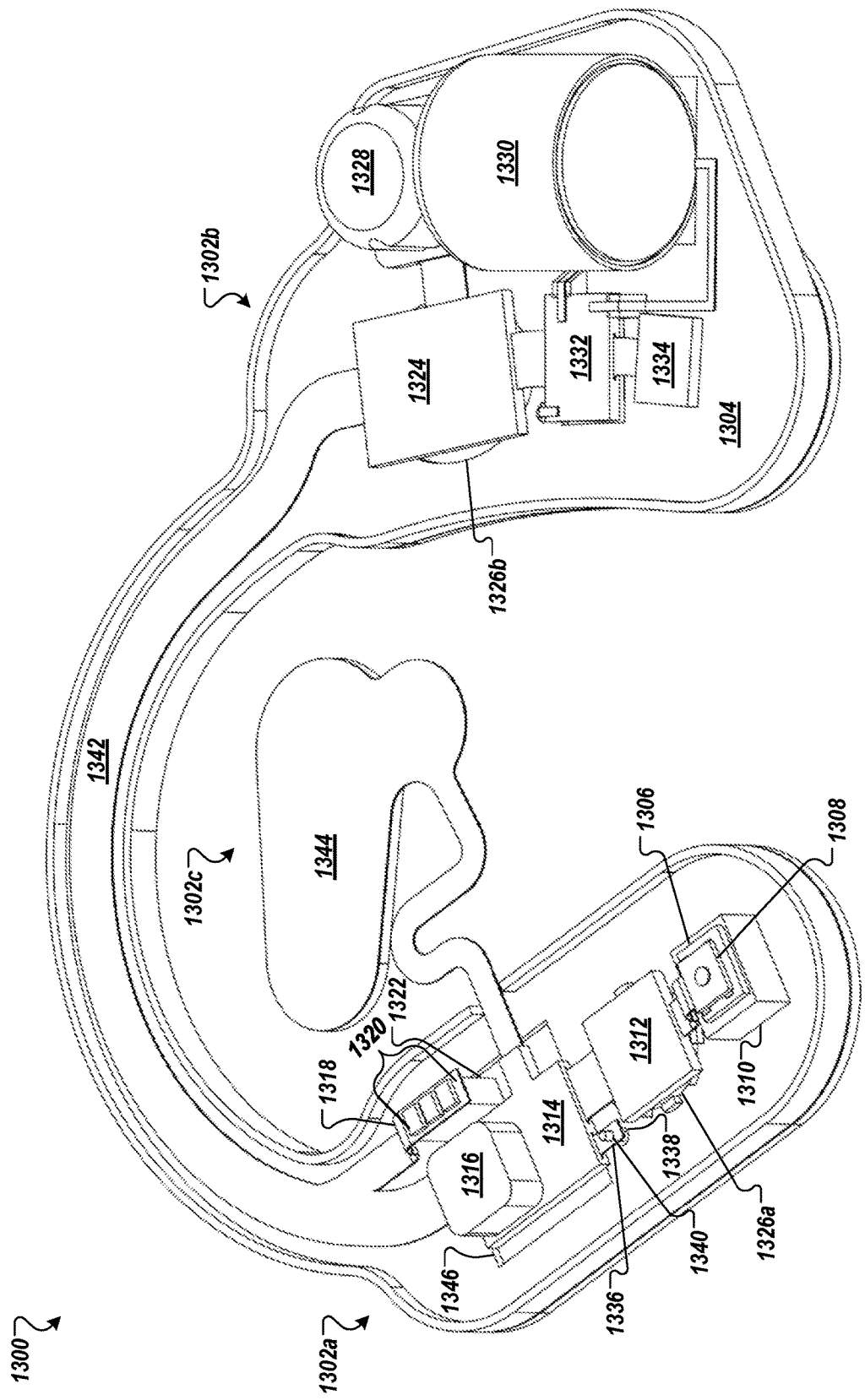
FIG. 13A illustrates a second example assembled WANS apparatus.

Turning to FIG. 13A, another example WANS apparatus 1300 is illustrated. Similar to the first example WANS apparatus 100 of FIG. 1, the WANS apparatus 1300 includes a forward portion 1302a, a rear portion 1302b, and an on-ear portion 1302c. The WANS apparatus 1300, in comparison to an internal view of the first example WANS apparatus 100 presented in FIG. 1, has replaced many of the smaller components of the WANS apparatus 100 with the same or similar functionality provided by a set of circuit components as illustrated in a flexible body portion 1304 of the WANS apparatus 1300. The circuit components, for example, may take place of certain printed circuitry components of the first example WANS apparatus 100 of FIG. 1. Further, certain circuit components may integrate one or more of the electronic components described in relation to the WANS apparatus 100 as described in relation to FIG. 2A through FIG. 2G. The circuit components, in some examples, may include flex circuitry printed circuit boards (PCBs), rigid-flex PCBs, and/or rigidized flex PCBs. Certain circuit components may be bent, curved, and/or folded to produce a three-dimensional surface area for the PCB, thereby allowing the circuit component to best fit within the three-dimensional structure of the flexible body portion 1302. Different circuit components may have different manufacturing types, for example based upon the type of circuitry and/or the positioning. In illustration, components which need to retain a position (e.g., a mechanical button or switch, an LED, etc.) may be formed as a less flexible (e.g., rigidized flex) or rigid circuit component, while components that are in a high-flex region (e.g., such as the portion of the WANS apparatus 1300 that wraps over the auricle) and/or require curving or folding to fit into an allocated position within the WANS apparatus 1300 may be manufactured as a flex circuitry component.

As illustrated, the forward portion 1302a of the example WANS apparatus 1300 includes an input circuit component 1306 topped by a mechanical control component (e.g., button switch) 1308. The flexible body portion 1304 includes a mounting platform 1310 for supporting the input circuit component 1306 with mechanical control component 1308. The mounting platform 1310, in some embodiments, is formed as part of the flexible body portion 1304. In other embodiments, the mounting platform 1310 is printed or placed within the flexible body portion 1304. For example, the mounting platform 1310 may be formed of a stiffer/more rigid material than the flexible body portion 1304 for retain positioning of the mechanical control component 1310 at the surface of a cover of the WANS apparatus 1300 (e.g., cover 1350 of FIG. 13B).

Figure 15A:
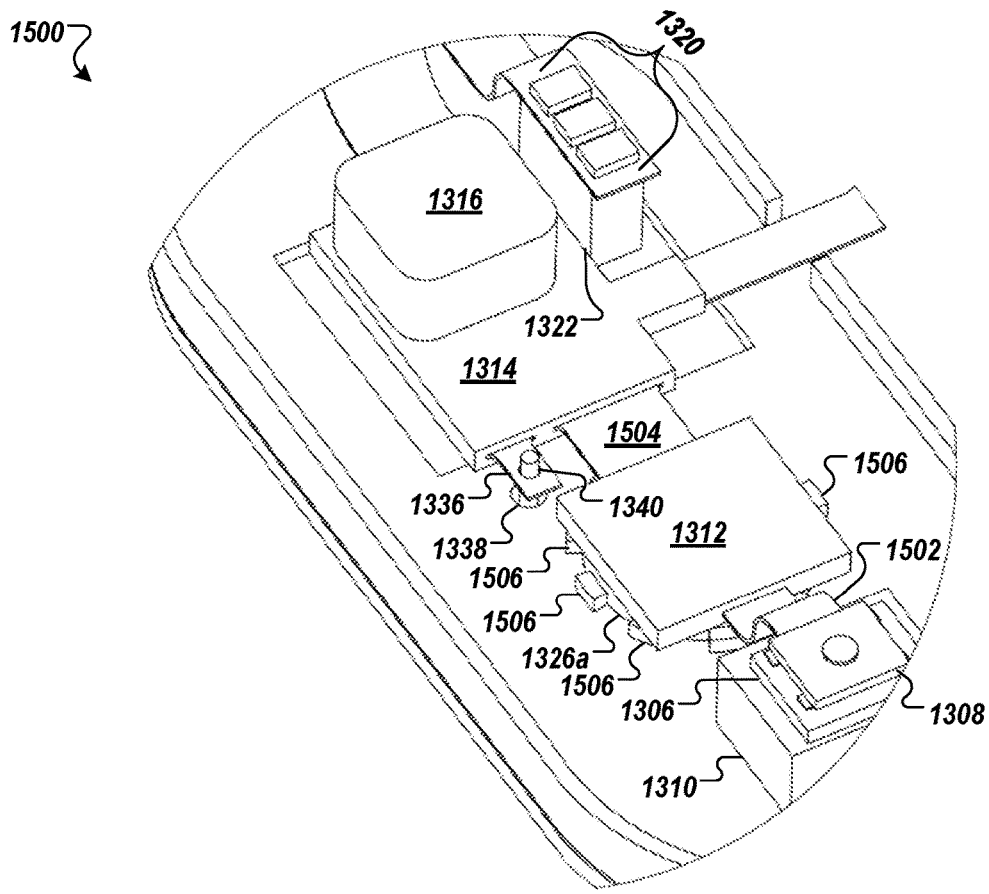
FIG. 15A through FIG. 15C illustrate detail view of portions of the internal components of the second example WANS apparatus.

As shown in a first detailed view 1500 of the WANS apparatus 1300 in FIG. 15A, the input circuit component 1306 is electrically connected to a circuit component 1312 by a three-dimensionally formed flexible circuitry bridge 1502. Flexible circuitry bridging components of the WANS apparatus 1300, for example, may include traces for each signal type carried by a particular device as well as power traces for delivering power throughout the components of the WANS apparatus 1300. The flexible circuitry bridging components, for example, may be connected to other (rigid-flex, rigidized flex, etc.) components by pin connections.

The circuit component 1312 of the forward portion 1302a, in some embodiments, includes various circuitry components (e.g., resistors, capacitors, etc.) for supporting functionality of the WANS apparatus. The circuit component 1312 is electrically connected, via a flexible circuitry bridging component 1504, to a processing circuitry component 1314.

In some embodiments, the circuit component 1312 is disposed on a rounded (e.g., circular) cavity 1326a having one or more flexible protrusions extending therefrom and/or surrounding the cavity 1326a. For example, the cavity 1326a may house and/or be surrounded by a pattern of small pillars, allowing the circuit component 1312 to slide against the flexible protrusions during flexing of the WANS apparatus 1300. The flexible protrusions, for example, may additionally create a frictional force maintaining movement of the circuit component 1312 to a limited region. The frictional element, in one example, may be produced at least in part through sandwiching the circuit component 1312 between two sets (e.g., an upper set and a lower set) of small flexible protrusions. In other embodiments, the frictional effect may be produced by a type of material (e.g., sticky, tacky, etc.) and/or finish (e.g., roughness and/or patterning) of the material of the flexible protrusion(s). As illustrated in FIG. 15A and FIG. 15B, for example, the cavity 1326a is surrounded by pillars 1506. The cavity 1326a and protrusions are described in greater detail below in relation to FIG. 14A through FIG. 14D.

The processing circuitry component 1314 (e.g., microcontroller), in some implementations, controls therapeutic neurostimulations delivered via electrodes of the forward portion 1302a, the rear portion 1302b, and the on-ear portion 1302c. The electrodes may be electrically connected to the processing circuitry component 1314, in some examples, via printed circuitry traces, an extension off of one of the circuitry and/or flex circuitry components, and/or pin connections with an electronic component.

As illustrated, for example, a pin 1340 extends through an extension 1336 of the processing circuitry component 1314 to connect at least one first electrode to the processing circuitry component 1314. The extension 1336, for example, may be a flex circuitry extension of the printed circuit board of the processing circuitry component 1314. The pin 1340 extends into an opening (e.g., via) 1338 in the flexible body 1304. In FIG. 15A, the first detailed view 1500 of the WANS apparatus 1300 illustrates the layout with better clarity. An electrode may be produced, for example, by three-dimensionally printing on a back side of the flexible body 1304, then filling the opening 1338 with conductive ink to secure the electrical connection with the processing circuitry component 1314. The conductive ink, once deposited as the electrode and filled via, for example, may be cured.

In another example, an on-ear flexible circuitry (e.g., flex circuitry, rigid-flex circuitry, rigidized flex circuitry, etc.) component 1344 connects to the processing circuitry component 1314 to provide power and communications to one or more electrodes on or in electrical communication with the on-ear flexible circuitry component 1344.

The processing circuitry component 1314, in another example, may be electrically connected (e.g., via printed circuitry traces) to an electrode of the rear portion 1302b. In some embodiments, the processing circuitry component 1314 may be indirectly connected to other electrodes via another circuit component, such as a power circuitry component 1324 of the rear portion 1302b.

As illustrated, an output electronics component 1316 is mounted to the top of the processing circuitry component 1314. The output electronics component 1316, in some examples, may be a haptic feedback component, a speaker component, and/or a lighting component. The output electronics component 1316, for example, may be controlled by the processing circuitry component 1314 to present vibrational and/or audible alerts to the wearer, such as a low battery alert or a therapy beginning alert. In some implementations, a treatment device includes one or more haptic feedback actuators between electrode pairs. The haptic feedback actuator(s), for example, may move from a first position to a second position in repetitive patterns to mask sensations felt by stimulation of the electrodes. The haptic feedback actuator(s) may be configured to isolate or electrically separate conductive shunting pathways between electrodes, for example between portions of conductive gel.

In some implementations, the processing circuitry component 1314 and an illumination circuitry component 1318 adjacently positioned in a rectangular cavity 1346. The cavity, for example, may allow connectors of the processing circuitry component 1314 to align with a bottom surface of the flexible body 1304, thereby avoiding unnecessary flexing of the flexible circuitry connector component 1342 or the on-ear flexible circuitry 1344.

The illumination circuitry component 1318, in some embodiments, provides lighted feedback to a user, for example indicating that the WANS apparatus 1300 is powered on, low on battery, and/or currently active in therapy. The illumination circuitry, in some embodiments, is supported by one or more protrusions (e.g., pillars or pedestals), such as a pillar 1322, to position the lighting adjacent a surface of the WANS apparatus 1300 and/or partially through a cover of the WANS apparatus 1300 (e.g., exposing one or more light emitting diode (LED) lamps 1320). In some embodiments the LEDs may be used to signal the output intensity of the WANS.

Turning to FIG. 15B, in a second detailed view 1510 of the WANS apparatus 1300, the illumination circuitry component 1318 is illustrated on the pillar 1322 (e.g., pedestal or platform), positioning the illumination circuitry component 1318 closer to the height of the output component 1316. As illustrated, a three-dimensionally curved branch 1342a of a flexible circuitry connector component 1342 connects the processing circuitry component 1314 and the illumination component 1318 to the circuitry of the rear portion 1302b. Returning to FIG. 13A, as illustrated, the flexible circuitry connector component 1342 connects to the power circuitry component 1324 or a transition circuitry component 1332 of the rear portion 1302b.

The power circuitry component 1324, in some implementations, manages power distribution to the circuitry and components of the WANS apparatus 1300. The power circuitry component 1324, as illustrated, is disposed over a rounded (e.g., oval) cavity (e.g., well, depression) 1326b. In some embodiments, the rounded cavity 1326b, sized smaller than the power circuitry component 1324, may provide the power circuitry component 1324 with a limited range of movement. The power circuitry component 1324 is in direct electrical communication with an inductor component 1328 disposed next to a battery 1330.

Figure 15B:
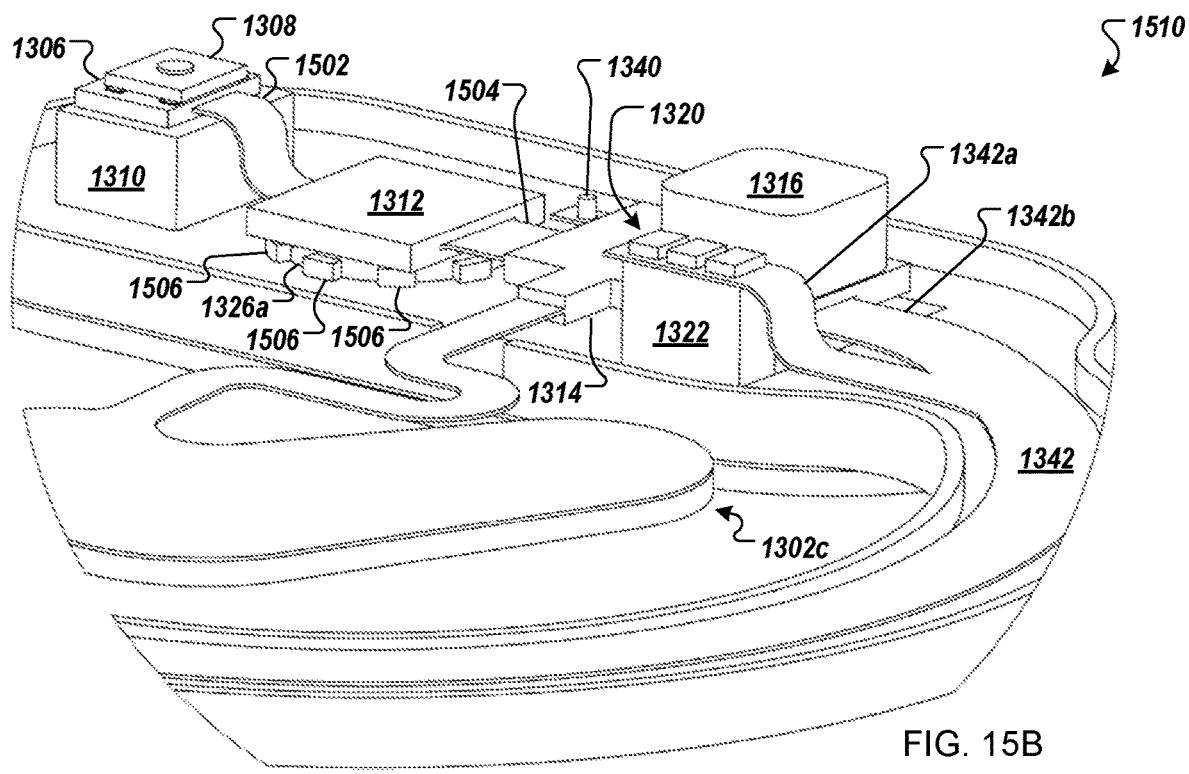
Figure 15C:
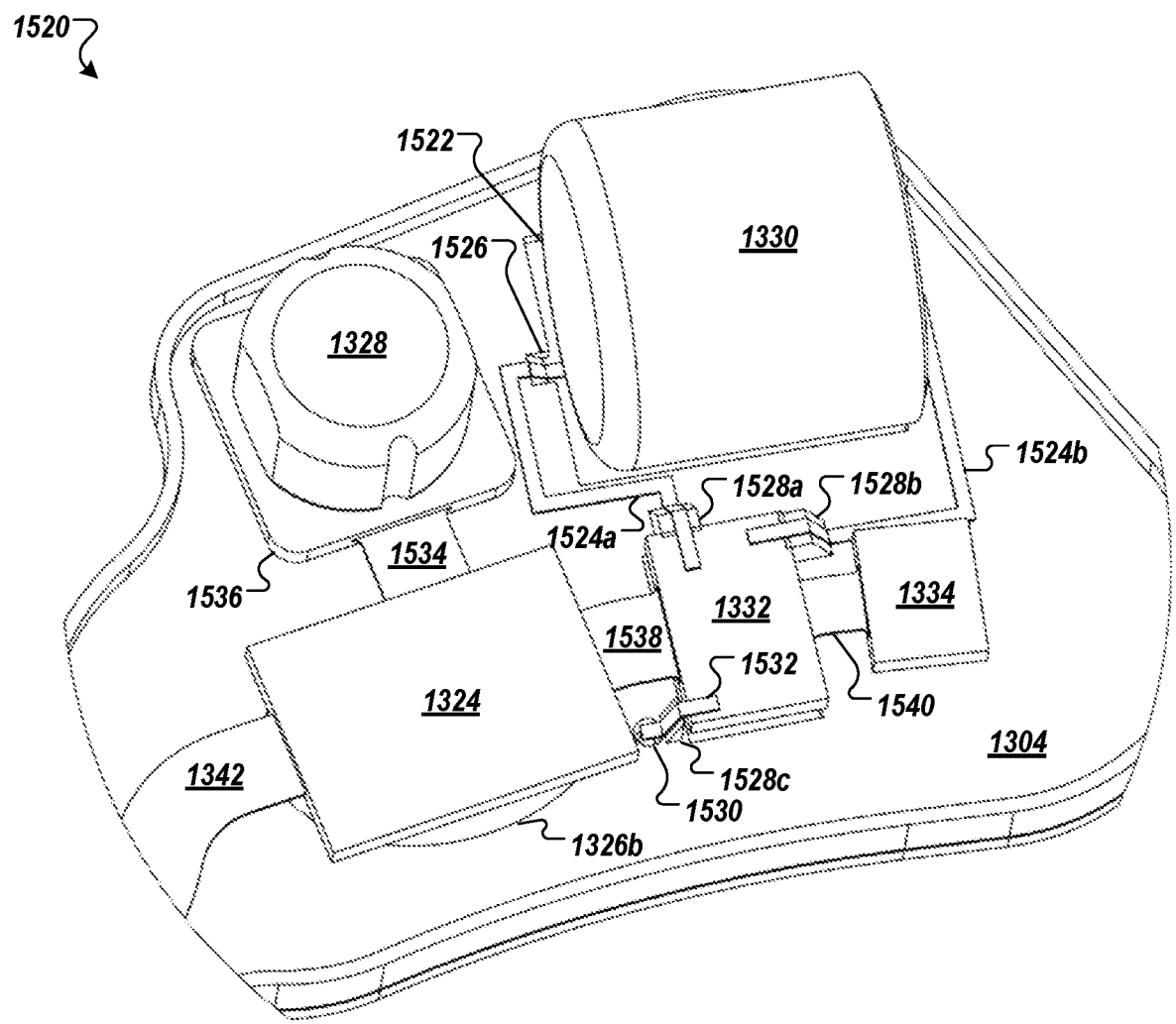

Turning to FIG. 15C, a third detailed view 1520 of the WANS apparatus 1300 illustrates the inductor component 1328 connected to the power circuitry component 1324 by a flexible circuitry connector 1534. In particular, the flexible circuitry connector 1534 is connected to an inductor circuitry component 1536 onto which the inductor 1328 is mounted.

As shown, the battery 1330 (e.g., a coin battery) is set in a rectangular cavity 1522. In some embodiments, the position of the battery 1330 is maintained by an adhesive deposited or otherwise placed in the cavity 1522.

In some implementations, the transition circuitry component 1332 (e.g., PCB) is connected, using three-dimensionally printed traces, to enable electrical communication between the battery 1330, the electrodes, and/or the circuit components (e.g., components 1306, 1312, 1314, 1318, and 1324). For example, turning to FIG. 15C, a printed circuitry trace 1524 electrically connects a transition circuitry component 1332 to the battery. A first portion of the printed circuitry trace 1524a travels from the transition circuitry component 1332, down an angled protrusion 1528a, along a lower surface of the flexible body 1304, and down a ramp 1526 into the cavity 1522 where it electrically connects to the battery 1330. A second portion of the printed circuitry trace 1524b exits the cavity via another ramp (not illustrated), travels along the lower surface of the flexible body 1304, and up an angled protrusion 1528b to the transition circuitry component 1332.

The transition circuitry component 1332, in some implementations, is also connected to a rear portion electrode through a via 1530. A printed circuitry trace 1532 travels down another angled protrusion 1528c from the transition circuitry component 1332 and over the via 1530. As with the pin 1340 illustrated in detail in FIG. 15A, an electrode may be printed on an exterior surface of the flexible body 1304 and the via 1530 filled with conductive material to create the electrical connection between the transition circuitry component 1332 and the electrode.

Flexible circuitry bridge components 1538 and 1540, respectively, connect the transition circuitry component 1332 to the power circuitry component 1324 and to a capacitor circuitry component 1334. The capacitor circuitry component 1334 may be provided to support the power circuitry component 1324.

Figure 13B:
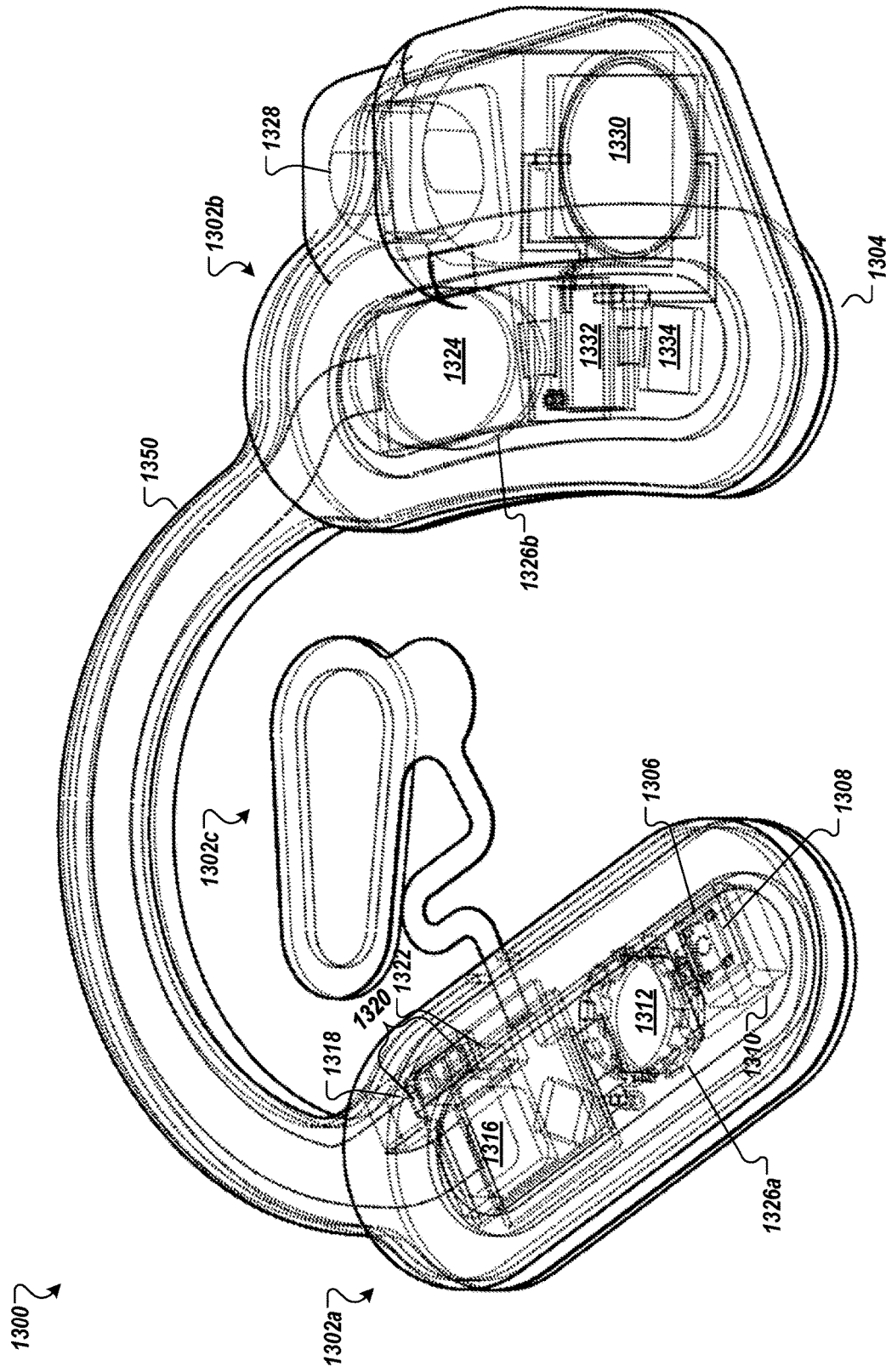
FIG. 13B illustrates internal components of the example WANS apparatus of FIG. 13A.
Figure 14A:
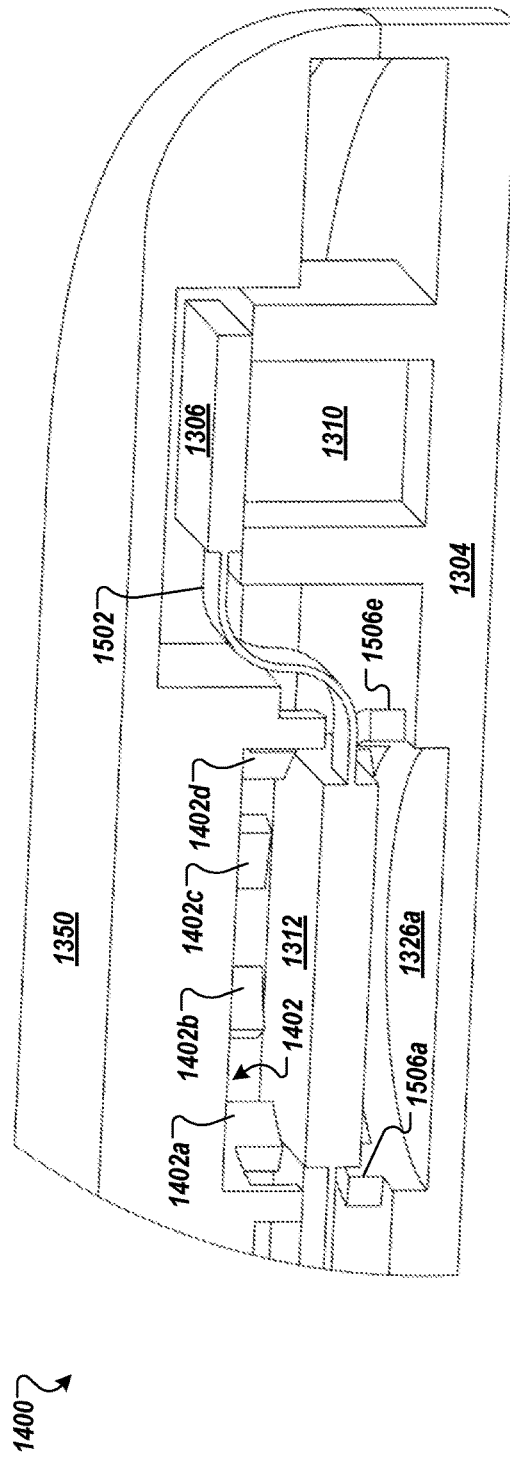
FIG. 14A through FIG. 14D illustrate cross-sectional views of an example WANS demonstrating limited freedom of movement of an electronic component.
Figure 14B:
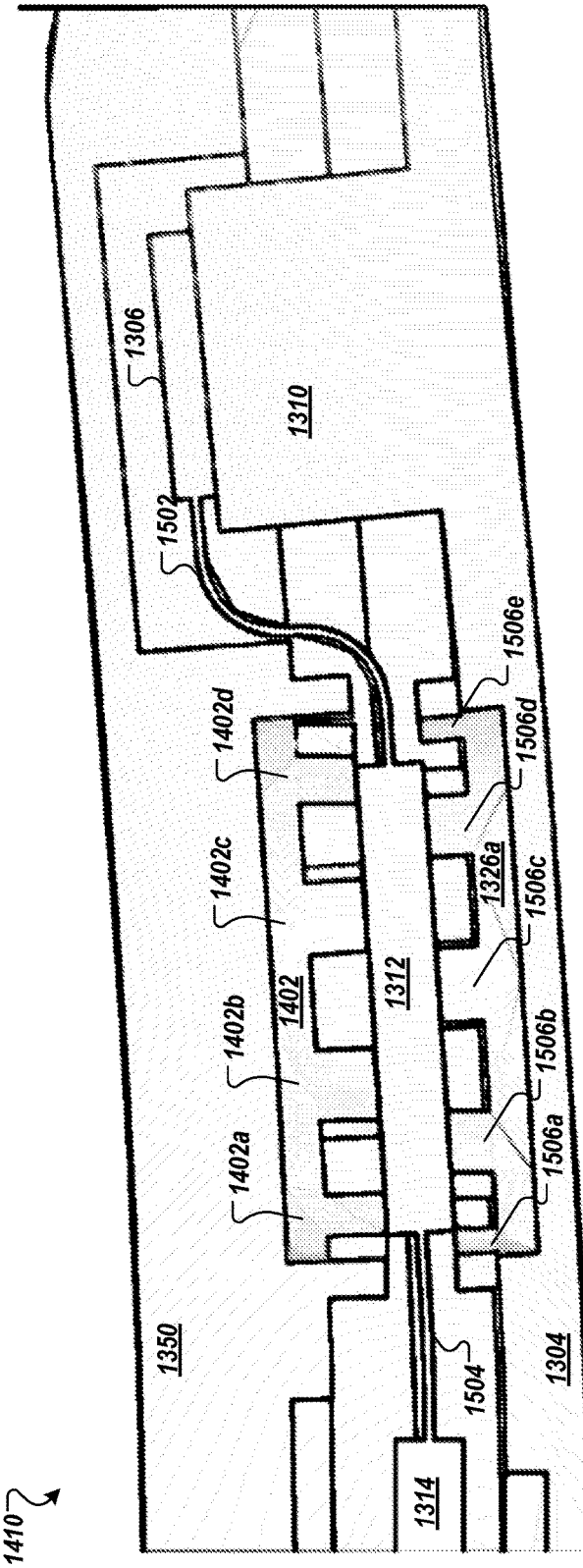

Turning to FIG. 14A, a first detailed cross-sectional view 1400 illustrates the circuit component 1312 suspended above the cavity 1326a by the ring of pillar components 1506. Additionally, upper pillar components 1402 extend downwards to connect with the circuit component 1312. The upper pillar components 1402, for example, may be formed upon or integrated into the cover 1350 of the WANS apparatus 1300. As illustrated, the upper pillar components 1402 surround an upper cavity 1404 in the cover 1350. Upon assembly of the flexibly body 1304 with the cover 1350, the combination of the lower cavity 1326a and the upper cavity 1404 provides a surrounding cavity region in which the circuit component 1312 is allowed limited movement. The rings of pillars in the flexible body 1304 and the cover 1350 are also visible in a see-through view of the WANS apparatus 1300 of FIG. 13B.

The upper pillar components 1402 and/or lower pillar components 1506, in some embodiments, are deformable and flexible such that they can respond to both lateral and compressive forces caused by flexing of the WANS apparatus 1300. For example, turning to a second detailed cross-sectional view 1410 of FIG. 14B, when the WANS apparatus 1300 is flexed in a region of the circuit component 1312, certain pillars may flex at an angle (e.g., as seen best with upper pillar 1402d and lower pillar 1506b). Further, certain pillars 1402 and/or 1506 may compress to adjust to forces exerted by the flexing of the WANS apparatus 1300.

Figure 14C:
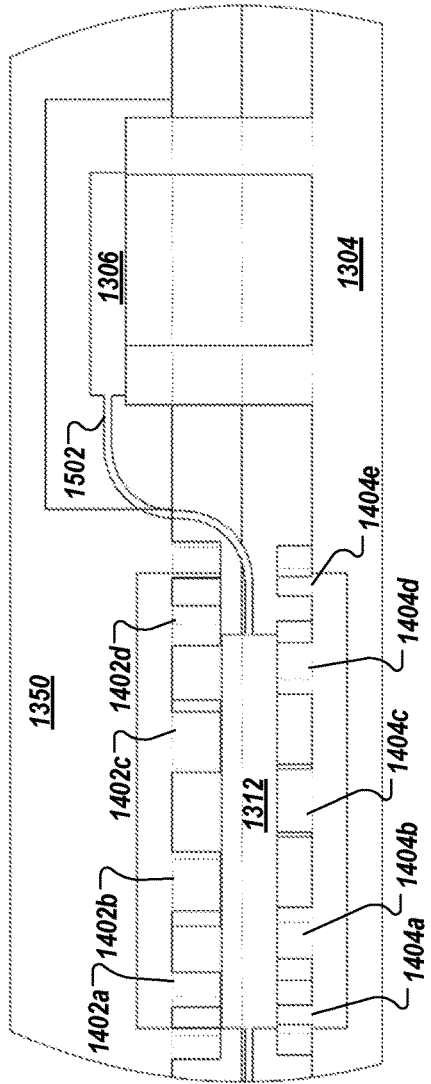
Figure 14D:
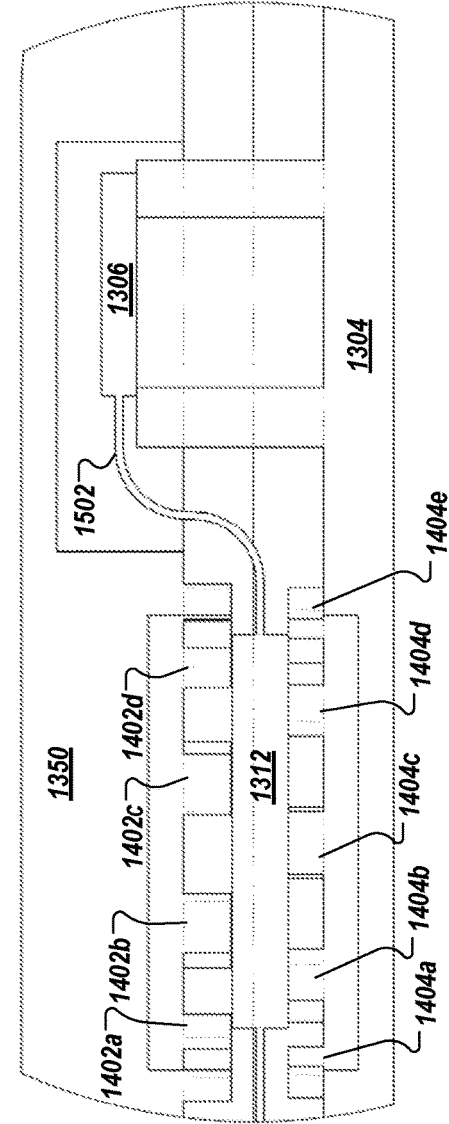

In some implementations, forces exerted on the WANS apparatus 1300, including flexing forces, compressive forces, and/or gravitational forces, result in the circuit component 1312 shifting back and forth (e.g., between the input circuit component 1306 and the processing circuitry component 1314). Turning to FIG. 14C and FIG. 14D, comparative cross-sectional views 1430 and 1440 of the WANS apparatus 1300 demonstrate an example range of lateral motion of the electronic component 1312.

Although described in relation to the electronic component 1312, generally, the design illustrated in FIG. 14A through FIG. 14D may be extended to other layouts of one or more compressible/deformable/flexible upper elements and a matching one or more compressible/deformable/flexible lower elements that provide a cavity for a component along with some range of motion for the component due to stresses placed on the WANS apparatus 1300. The mobility retention features provided by sandwiching a component between upper flexible element(s) and lower flexible element(s), for example, may protect connections from breaking and/or aspects of the components themselves from becoming damaged during use of the WANS apparatus 1300.

In embodiments beyond those illustrated in FIG. 14A through FIG. 14D, different shapes and sizes of pillars and/or cavities may be used, such as pillars arranged within the oval cavity 1326b of FIG. 13A, beneath the power circuitry component 1324. In further embodiments, no cavity may be provided. For example, two raised regions may instead provide a "nest" into which a component may be placed.

The pillars, although illustrated as rectangular blocks, could, in other implementations, be formed as circular columns, hexagonal columns, or other shapes. Further, the columns, in some implementations, may be tapered (e.g., a rounded or cut-off cone or pyramid, etc.).

Rather than pillars, in some implementations, a region of flexible material may be cut or scored to provide movement. In illustration, a raised ring formed, for example, like a doughnut may be cut into slits to allow for flexing and/or bending. In other implementations, a matching pair of solid flexible doughnut shaped regions (e.g., body portion 1304 and cover 1350) may be provided to allow for deformation during flexing or pending and some sliding maneuverability.

Figure 7A:
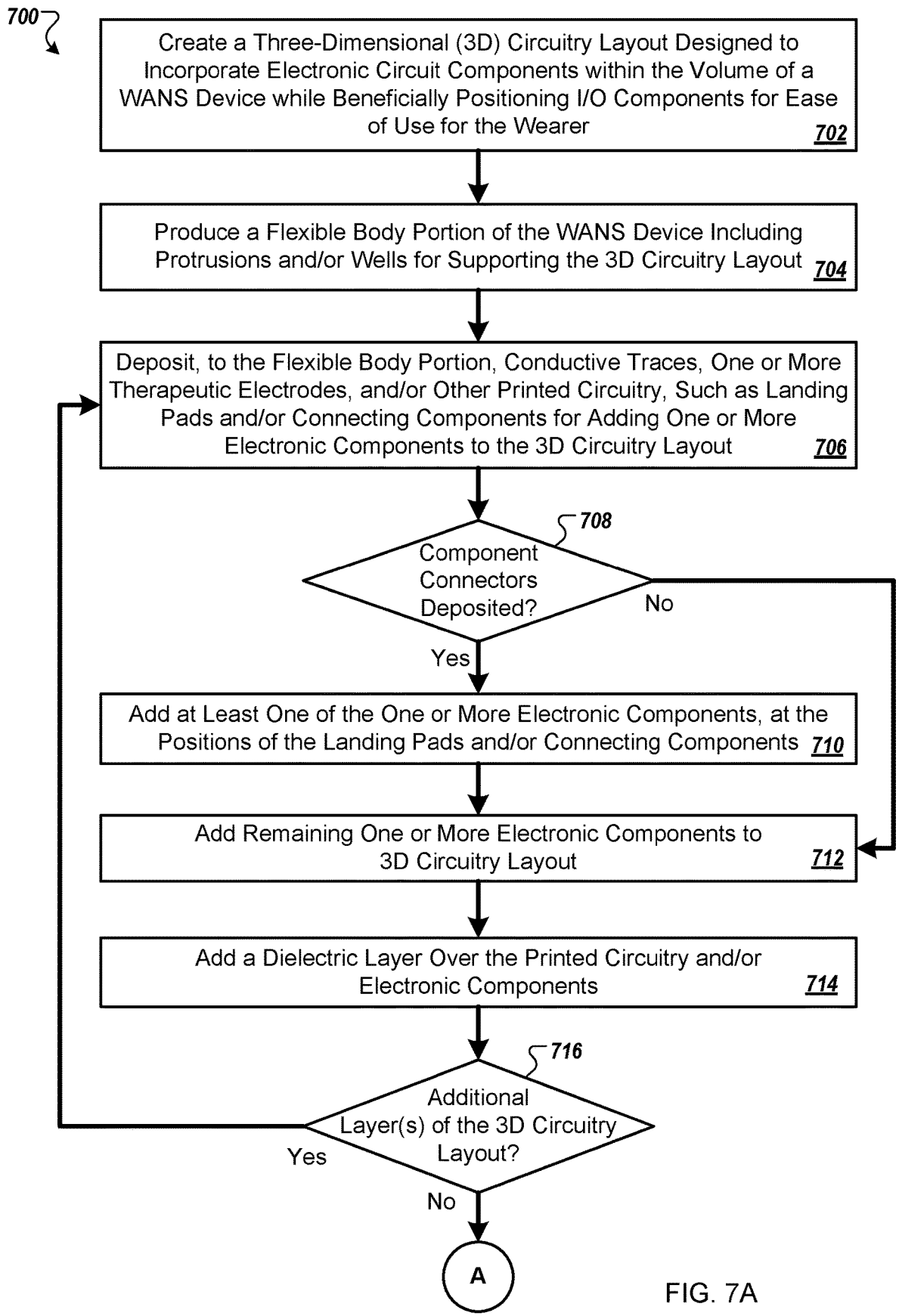
FIG. 7A and FIG. 7B illustrate an example method for manufacturing a WANS apparatus having three-dimensionally printed flexible circuitry.
Figure 7B:
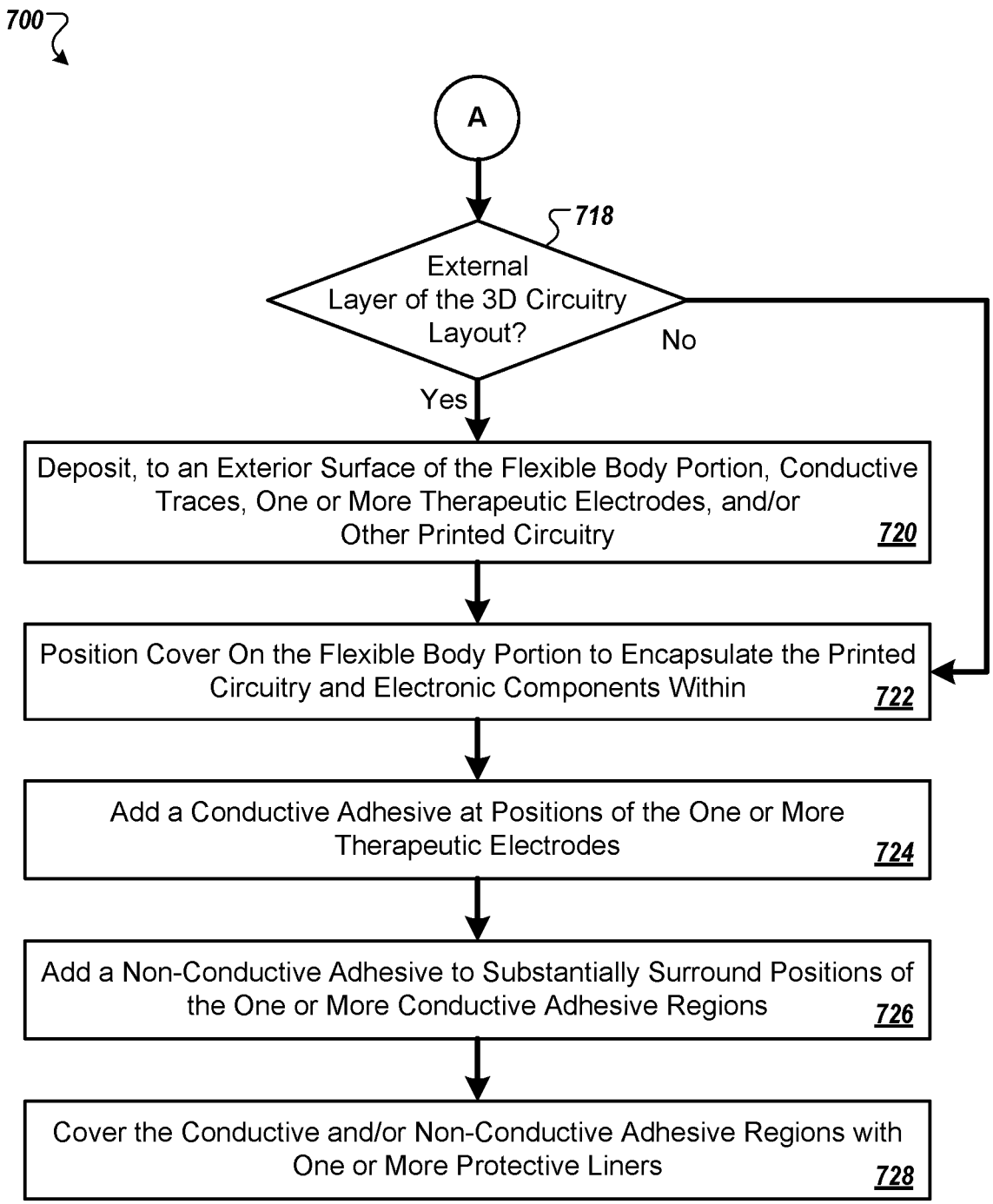

FIG. 7A and FIG. 7B illustrate a flow chart of an example method 700 for manufacturing a WANS device, such as the device 100 of FIG. 1, the device 500 of FIG. 5, and/or the device 1300 of FIG. 13B.

In some implementations, the method 700 begins with creating a three-dimensional (3D) circuitry layout designed to incorporate electronic circuit components within the volume of a WANS device while beneficially positioning I/O components for ease of use of the wearer. In some embodiments, a rigid or a rigid-flex PCB containing multiple electronic components is treated as a single electronic component and incorporated as such into the WANS 3D circuitry layout. Further, in some embodiments, a flexible circuitry connector comprising electrical trace connections for transferring signals from one circuitry component to another circuitry component may be treated as an electronic component. The 3D circuitry layout, for example, may be designed using a computer-aided design software package.

In some implementations, a flexible body portion of the WANS device including protrusions and/or wells for supporting the three-dimensional circuitry layout is produced (704). The flexible body portion, for example, may be produced as described in relation to the body portion 102 of FIG. 1. The protrusions and/or wells, for example, may be produced in a manner similar to that described in relation to the protrusions 208 and/or wells 210 of FIG. 2A. The flexible body portion may be produced to have one or more openings for therapeutic electrode communication and/or access to I/O circuit elements. The openings, for example, may be similar to the openings 204 of FIG. 2A. In some embodiments, one or more openings are created in the flexible body portion after production. In some examples, one or more openings may be punched or laser cut from a molded or printed part.

In some implementations, conductive traces, therapeutic electrodes, and/or other printed circuitry are deposited upon the flexible body portion (706). The printed circuitry, for example, may be deposited as described in relation to the printed circuitry 104 of FIG. 1, the printed circuitry illustrated in FIG. 2B, and/or the printed circuitry 300 of FIG. 3. The printed circuitry may include one or more therapeutic electrodes, such as the electrodes 220a and 224 of FIG. 2B, the electrode 222a of FIG. 2F, and/or the electrodes 306a, 308a, and 310 of FIG. 3. The printed circuitry may include one or more landing pads and/or connecting components (e.g., the electrical contacts 226a-n of FIG. 2B) for adding one or more electronic components to the 3D circuitry, such as the electronic components 106 of FIG. 1.

In some implementations, if any connecting components and/or landing pads were provided (708), at least one of the one or more electronic components are added to the printed circuitry at the positions of the landing pads and/or connecting components (710). Adding the electronic components may include soldering, inserting, and/or adhering each component. Certain components may be automatically added to the printed circuitry, while other components may be manually added to the printed circuitry. The electronic components, for example, may be added as described in relation to the electronic components 106 of FIG. 1.

In some implementations, any remaining electronic components are added to the 3D circuitry layout (712). For example, the circuit components and the flexible circuitry connectors of the 3D circuitry layout of the WANS apparatus 1300 of FIG. 13A may be added.

In some implementations, a dielectric layer is added over the printed circuitry and/or the electronic components (714). The dielectric layer, in some examples, can be printed, 3D printed, and/or sprayed onto the printed circuitry and/or electronic components. The dielectric layer, for example, may insulate the printed circuitry and/or electronic components from short-circuiting, cross-talk, and/or signal delay. The dielectric layer may further provide thermal conductivity to avoid overheating of the circuitry components.

In some implementations where the three-dimensional circuitry layout includes two or more layers (716), one or more of operations 706 through 714 may be repeated. For example, the added dielectric layer (714) can be used to isolate multiple layers of conductive traces allowing them to cross each other over different layers. As illustrated in FIGS. 2D and 2E, for example the electronic components may be added in one or more layers on top of the printed circuitry. In another example, additional traces may be added after positioning of certain electronic components to interlink certain components and/or to connect certain components to other features of the printed circuitry (e.g., electrodes, landing pads, etc.), such as the traces 1524 and 1532 connecting to the transition component 1332 as illustrated in FIG. 15C. After depositing the traces 1524 and 1532, for example, the battery 1330 may be added (710) to the 3D circuitry layout of the WANS device 1300 of FIG. 13A.

In some implementations, if the 3D circuitry layout includes an external layer on an exterior surface of the flexible body portion (718), conductive traces, one or more therapeutic electrodes, and/or other printed circuitry are deposited to an exterior surface of the flexible body portion (720). For example, the electrodes may be formed and vias 1338 and 1530 filled as described in relation to FIG. 13A and FIG. 15C.

In some implementations, a cover is positioned on the flexible body portion to encapsulate the printed circuitry and electronic components within (722). The cover may be formed of a same or similar material as the flexible body portion. In some examples, the cover may be molded, overmolded, and/or three-dimensionally printed. In some embodiments, the cover includes one or more features, such as one or more seals and/or drainage paths, for providing a water-resistant or waterproof seal with the flexible body portion. The cover, for example, may be designed in a similar manner as the cover 108 of FIG. 1.

Figure 6:
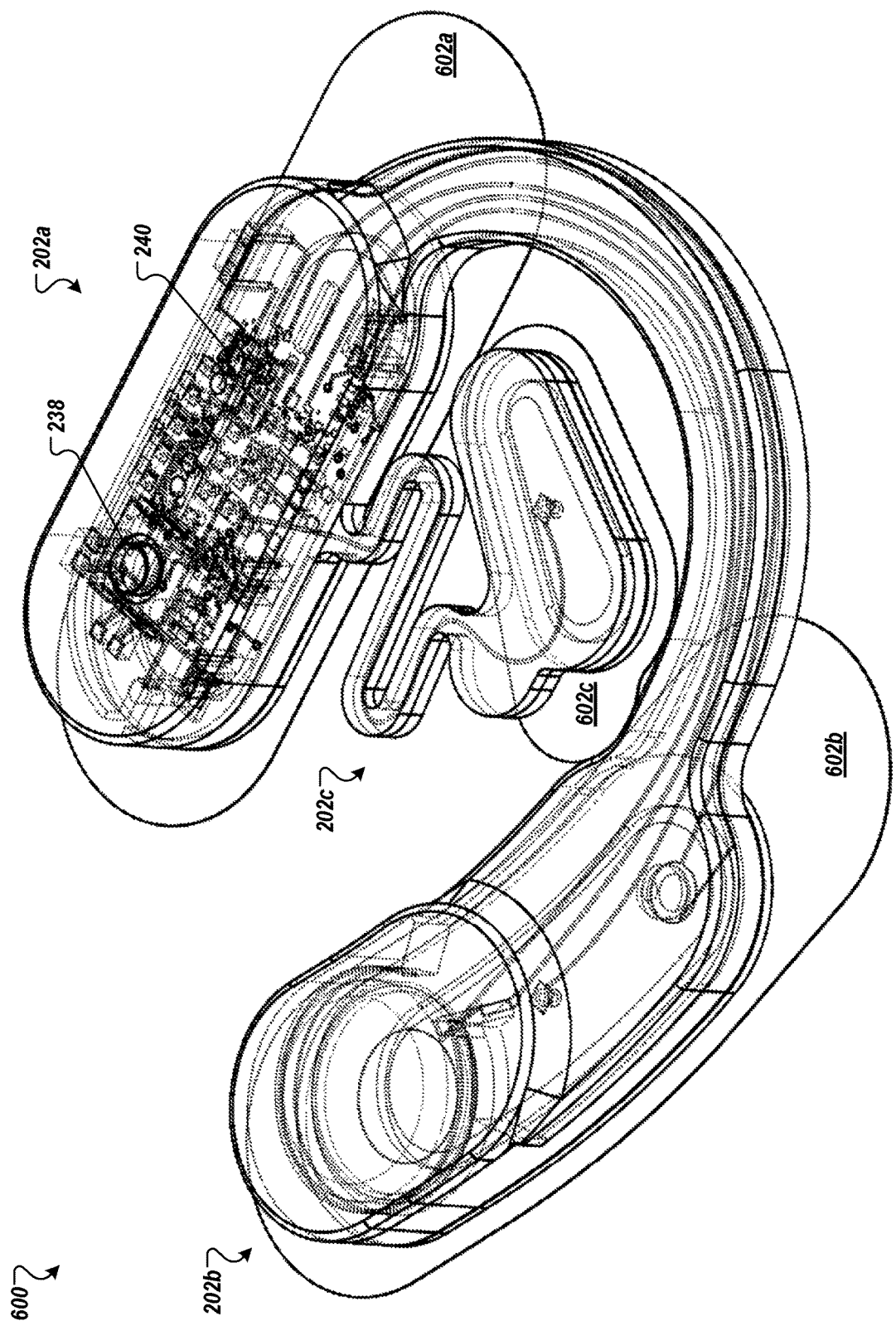
FIG. 6 illustrates an example assembled WANS apparatus.

In some embodiments, the cover includes one or more openings, such as the openings 404 and 406 of the cover 400 of FIG. 4. Positioning the cover may include aligning the opening(s) of the cover with one or more features of the printed circuitry and/or electronic components. Turning to FIG. 6, a diagram of a transparent fully assembled WANS apparatus 600 is illustrated to demonstrate positioning of the various components and circuitry illustrated in FIG. 2A through FIG. 2E within. As illustrated, the button 238 and the LED 240 are exposed by openings in the cover (e.g., the cover 400 of FIG. 4). In other embodiments, the material of the cover is made thinner at specific areas such that, for example, LED 240 or multiple LEDs can be seen through a remaining thickness of the material of the cover when illuminated without an actual opening, thus keeping the interior of the WANS sealed.

Turning to FIG. 7B, in some implementations, a conductive adhesive is added to the positions of the one or more therapeutic electrodes (724). Additionally, as discussed in relation to FIG. 3 and FIG. 5 the electrodes may include a return electrode. The conductive adhesive, for example, may be added in one or more of the manners described in relation to the conductive adhesive 110 of FIG. 1. Although illustrated in relation to the flexible portion, in certain embodiments, conductive adhesive may be added to the positions of one or more electrodes aligned with the cover of the WANS device.

In some implementations, a non-conductive adhesive is added to substantially surround the positions of the one or more conductive adhesive regions (726). The non-conductive adhesive, for example, may be added in one or more of the manners described in relation to the non-conductive adhesive 112 of FIG. 1. The non-conductive adhesive may partially or fully surround the conductive adhesive as described and illustrated in relation to FIG. 5. Although illustrated in relation to the flexible portion, in certain embodiments, non-conductive adhesive may be added to around positions of one or more conductive adhesive regions added to the cover of the WANS device.

In some implementations, the adhesive regions (e.g., conductive and/or non-conductive) of the WANS device are covered with one or more protective liners (728). The liners may maintain adhesion quality and cleanliness of the adhesive regions of the device until such time that the device is to be worn. The liners, for example, may be provided as described in relation to the liners 114 of FIG. 1 and/or the liners 514a, 514b of FIG. 5. In another example, as illustrated in FIG. 6, a forward liner 602a, a rear liner 602b, and an in-ear portion liner 602c are provided to cover adhesive portions.

In an illustrative example, a treatment device such as the device 100 of FIG. 1 or the device 1300 of FIG. 13 may be donned as follows. In implementations having protective liners on the skin adhesive and/or electrodes, remove the protective liners before use. Apply the auricular component around the auricle of the patient and press against the patient's skin such that exposed skin adhesives and adhesives/hydrogels (or other conductive adhesive) adhere to the skin. Next, place the on-ear component in the ear such that at least a portion of the on-ear is positioned outside the external ear canal in the cavum and/or engages with the cymba of the ear.

Electrodes can be made larger or combined such that, for example, multiple electrodes are combined into one large contact, such as the contact pads 804a, 804b, and 804c. A treatment device, in some embodiments, includes a set of electrodes configured to be virtually grouped together to form one or more effective electrodes. For example, a first grouping of electrodes can be equivalent to electrode 804a, a second grouping of electrodes can be equivalent to electrode 804b, and a third grouping of electrodes can be equivalent to electrode 804c. Grouping smaller electrodes provides the ability to have multiple electrodes each with its own independently controlled current source, allowing for current steering, thereby providing better spatial resolution and targeting capabilities. Electrodes may be virtually grouped by processing circuitry.

Although the method 700 is described in relation to a particular series of operations, in other embodiments, more or fewer operations may be included in the method 700. For example, in other embodiments, rather than positioning a cover (722), a second flexible body portion may be produced which is designed to mate with the first flexible body portion to complete connection of shared circuitry between flexible body portions. In certain embodiments, one or more of the operations may be performed in a different order or in parallel. For example, the conductive adhesive and non-conductive adhesive may be added (724, 726) in a different order and/or concurrently.

Although the WANS apparatus 100 of FIG. 1, the WANS apparatus 500 OF FIG. 5, and the WANS apparatus 1300 of FIG. 13A are each described as a device worn on a single ear of a patient, other forms of WANS apparatus may be constructed using the general operational flow of the method 700, such as a device worn on both ears of the patient or a device having a flexible body portion and three-dimensional circuitry for delivering therapy to other portions of a wearer's face and/or neck, such as a band designed to contact a wearer's temples and/or jaw line. In the illustrative example including two auricular units, the WANS apparatus may be printed in a similar manner, although including the same or similar elements for flexible body portions for each ear (e.g., substantially a mirror image). Further to the example, the two flexible body portions may be connected via a band or cord. The band or cord may be molded and/or printed in a manner similar to that described in relation to the flexible body portion (704). The flexible body portions, for example, may be connected by a stretchable "telephone cord" curled band, a flat stretchable band, a flat semi-rigid band, or other physical connection interlinking the two flexible body portions. Rather than creating a continuous apparatus having two auricular units and a connector (e.g., band, cable, cord, etc.), in some embodiments, two separate auricular units may each be mounted to or plugged into a shared connector. For example, to assist in adjustment of the auricular units against the ear, each auricular unit may be pivotally or rotationally mounted to a connector (e.g., using a ball joint, a rotating hinge, etc.). The three-dimensional circuitry layout may be designed (702) to include a master flexible body portion including a controller configured to deliver a coordinated therapy between the two ear portions. In another example, the WANS apparatus may include two separate ear-mounted devices formed in a manner as described in relation to the method 700, with at least one of the ear-mounted devices including control circuitry and each ear-mounted device including wireless communication circuitry for coordinating delivery of therapeutic pulses.

Figure 11:
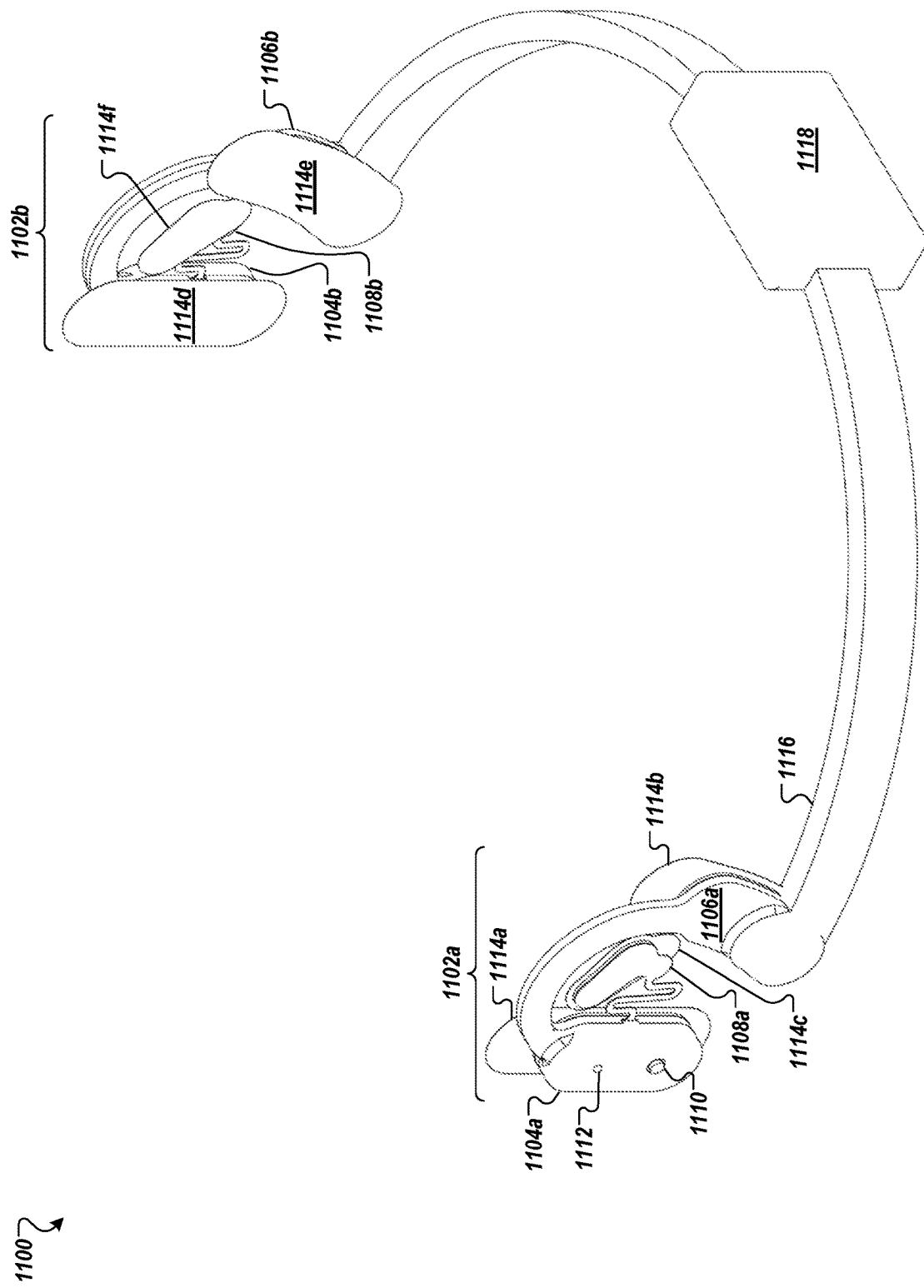
FIG. 11 illustrates an example WANS apparatus including two auricular units connected by a band.

Turning to FIG. 11, an example WANS apparatus 1100 includes two auricular units 1102a, 1102b connected by a band 1116 configured to be worn around the back of a wearer's head (e.g., against the occiput). Similar to the WANS apparatus 100 described in relation to FIG. 2A through FIG. 2E, each auricular unit 1102 of the WANS apparatus 1100 includes a forward portion 1104, a rear portion 1106, and an on-ear portion 1108. As illustrated the left side auricular unit 1102a includes a control button 1110 and an indicator lamp 1112. Skin-facing surfaces of the forward portions 1104a, 1104b, the rear portions 1106a, 1106b, and the on-ear portions 1108a, 1108b are protected with liners 1114a-f.

In some implementations, a control housing 1118 is positioned on the band 1116. The control housing 1118, in some embodiments, includes control circuitry for delivering therapeutic pulses via electrodes of the auricular units 1102a, 1102b. In some embodiments, the control housing 1118 includes a wireless communications unit for receiving control instructions from a separate device. For example, a pulse generator component of the control housing 1118 may be controlled by instructions delivered via wireless communications. The control housing 1118 may further include power circuitry, such as a battery unit, for delivering power to the auricular units 1102a, 1102b.

Figure 12:
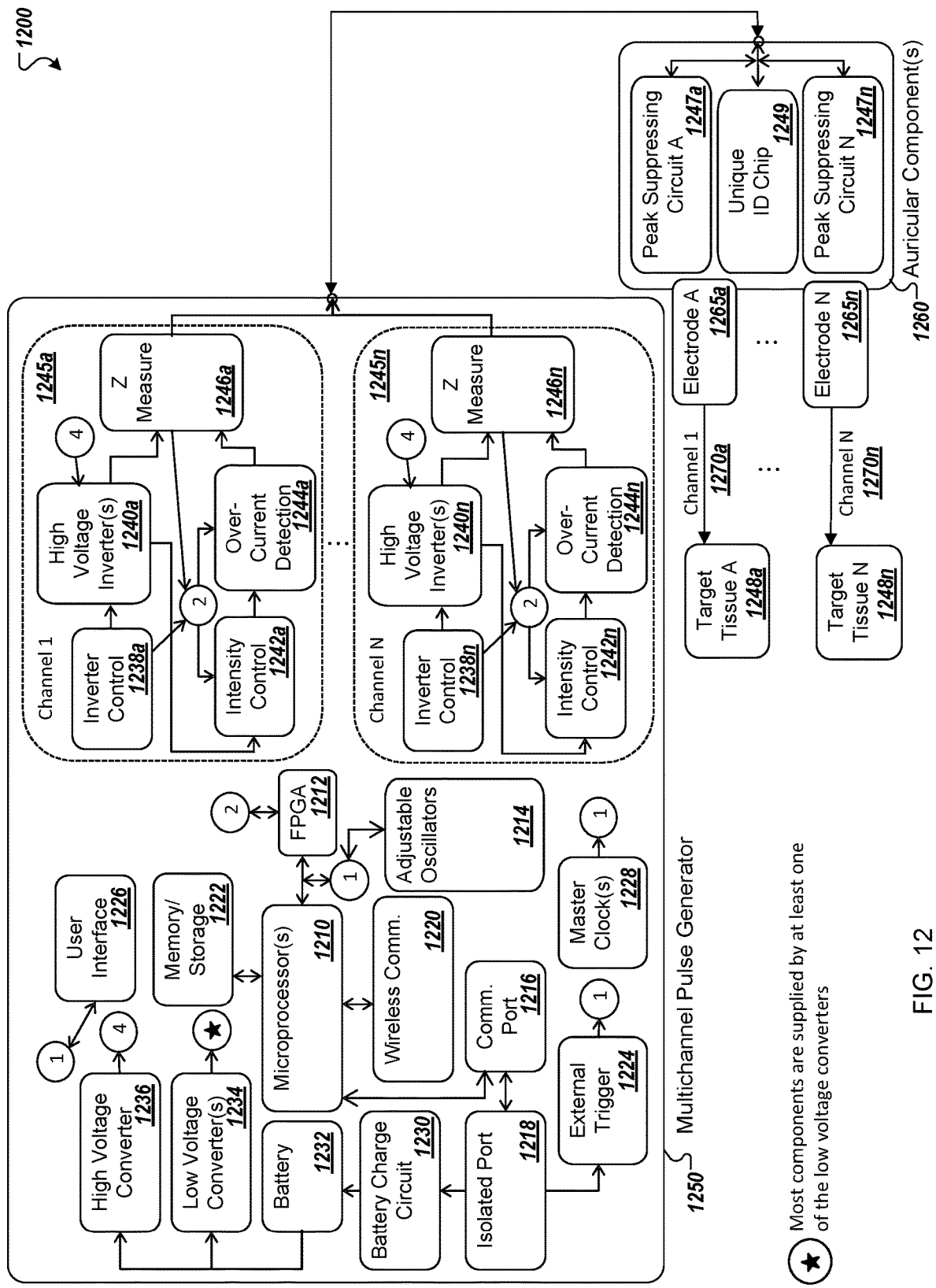
FIG. 12 illustrates a block diagram of components of an example pulse generator in communication with an example auricular therapy device.

Turning to FIG. 12, a block diagram 1200 of example components of a pulse generator 1250 in communication with example components of an auricular component 1260 is shown. The multichannel pulse generator circuit 1250, in some embodiments, has at least one microcontroller or a microprocessor 1210 with at least one core. When multiple microcontrollers or multiple cores are present, for example, one may control the wireless communication 1220 and other core(s) may be dedicated to control the therapy. In some implementations, a low power programmable logic circuitry (e.g., field programmable gate array (FPGA) or programmable logic device (PLD)) 1212 is also provided. For example, the microcontroller 1210 may be configured to switch into a low power mode as frequently as possible while the programmable logic circuitry 1212 controls therapy delivery.

In some embodiments, an inverter circuit 1245*a-n* is used to generate biphasic/bipolar pulses. In some embodiments, one inverter circuit 1245*a-n* is used per channel 1270*a-n*, while in other embodiments, a single inverter circuit 1245 is used for multiple channels 1270*a-n*. Each channel 1245*a-n*, for example, may target a different anatomical area (e.g., tissue region) 1248*a-n*. A high voltage compliance (e.g., >50V, in other embodiments >70V, and yet in others >90V) may be used to ensure there is enough margin on the electrical potential to generate current demanded by the intensity control 1242*a-n* of each inverter circuit 1245*a-n* by providing one or more high voltage inverters 1240*a-n* per inverter circuit 1245*a-n*. In order to enhance safety, in some embodiments, an over current detection circuit 1244*a-n* is provided in each inverter circuit 1245*a-n*. In some embodiments, an impedance measuring circuit 1246*a-n* is provided in each inverter circuit 1245*a-n*. The impedance measuring circuit 1246*a-n*, for example, may support tracking impedance over time to identify failure of sufficient therapy delivery. In some examples, therapy delivery may be compromised when the electrodes are not in contact or in good contact with the target tissue 1248*a-n*, when a cable or connector between the multichannel pulse generator 1250 is disconnected from one of the auricular component(s) 1260, or where the electrodes have deteriorated or are defective. Monitoring impedance over time provides the added advantage that the condition of the contact electrode can be followed; thus allowing the controller to alert the user when the contact electrodes are close to their end of life or no longer viable. The FPGA 1212 may control the inverter circuits 1245*a-n* and receive feedback from an inverter control component 1238*a-n*.

In some implementations, a battery 1232 is used to power the pulse generator 1250. The battery 1232, for example, may power components of the pulse generator 1250 and/or the auricular component(s) 1260 via a one or more low voltage converters 1234. Further, the pulse generator 1250 may include a high voltage converter 1236, coupled to one or more high voltage inverters 1240*a*-1240*n*, for delivery electrical stimulation therapy via the one or more channels 1245*a-n*.

In some embodiments, an isolated port 1218, such as a universal serial bus (USB) is used to charge the battery 1232 (e.g., via battery charge circuit 1230), and to communicate with the microcontroller(s) 1210 (e.g., via a communications port 1216). The communication can be both ways, such that instructions or entire new code can be uploaded to the microcontroller(s) 1210 and information stored in a memory 1222 may be downloaded. In some embodiments, the memory 1222 or additional memory can be added to the circuitry as an external component (e.g., in wireless or wired communication with the pulse generator 1250). For example, the isolated port 1218 (e.g., USB) may be used to connect memory to the pulse generator 1250. In other embodiments, at least portions of the memory 1222 may be internal to the microcontroller(s) 1210. In some embodiments, the FPGA 1212 may also have internal memory.

In some embodiments, an external trigger circuit 1224 is included, such that the stimulation can be started and/or stopped via an external signal. In some embodiments, the external trigger signal can be passed through the isolated port 1218; in yet other embodiments a modified USB configuration (i.e., not using the standard USB pin configuration) can be used to pass the trigger signal. Using a modified USB configuration will force a custom USB cable to be used, thus ensuring that an external trigger cannot be provided by mistake using an off-the-shelf USB cable. In a further example, the external trigger signal may be wirelessly transmitted (e.g., by Bluetooth) from a separate source.

In some embodiments, a hardware user interface is provided for interacting with the multichannel pulse generator 1250 via user interface circuitry 1226. In an example, the user interface circuitry 1226 can include of buttons, LEDs, haptic (e.g., piezoelectric) devices such as buzzers, and/or a display, or a combination of any of them. In some embodiments, the user interface circuitry 1226 includes signal processing components for interpreting user interface commands delivered via an external device (e.g., through the wireless communications 1220). The external device, in some examples, may be a smart phone app, a tablet computer, or a medical monitoring device (e.g., in a hospital setting).

In some embodiments, an external master clock 1228 is used to drive the microcontroller(s) 1210 and/or the FPGA 1212. In other embodiments the clock(s) of the components can be internal or integrated or co-packaged with the microcontroller(s) 1210 and/or the FPGA 1212. In some embodiments, one or more oscillators, including in some cases adjustable oscillators 1214 are used to set pulse parameters such as, for example, frequency and/or pulse width.

In some embodiments, the auricular component 1260 is made from a thin flex PCB or printed electronics, such that it is light weight and can be easily bent to accommodate different anatomies. In some embodiments, the auricular component 1260 has more than one channel. The auricular component 1260, or each channel thereof, may include a peak suppressing circuit 1247*a-n* and electrodes 1265*a-n* to contact the skin at the location of the target tissue 1248*a-n*. In some embodiments, the auricular component(s) 1260 includes a unique chip identifier or unique ID chip 1249. The unique ID chip can be used to track usage as well as to prevent other non-authorized circuits from connecting to the multichannel pulse generator 1250. At least one auricular component(s) 1260 is connected to the multichannel pulse generator 1250.

In an exemplary embodiment, the system utilizes feedback to monitor and/or modify the therapy. The feedback may be obtained from one or more sensors capable of monitoring one or more symptoms being treated by the therapy. For example, upon reduction or removal of one or more symptoms, a therapeutic output may be similarly reduced or ceased. Conversely, upon increase or addition of one or more symptoms, the therapeutic output may be similarly activated or adjusted (increased, expanded upon, etc.). In some examples, the sensors may monitor one or more of electrodermal activity (e.g., sweating), movement activity (e.g., tremors, physiologic movement), glucose level, neurological activity (e.g., via EEG), muscle activity (e.g., via EMG) and/or cardio-pulmonary activity (e.g., EKG, heart rate, blood pressure (systolic, diastolic, and/or mean)). Imaging techniques such as MRI and fMRI could be used to adjust the therapy in a clinical setting for a given user. In other embodiments, imaging of pupillary changes (e.g., pupillary dilation) using, for example a common cellular phone and/or smart-glass glasses could be used to provide feedback to make therapy adjustments. In some implementations, one or more sensors are integrated into the earpiece and/or concha apparatus. One or more sensors, in some implementations, are integrated into the pulse generator. For example, periodic monitoring may be achieved through prompting the wearer to touch one or more electrodes on the system (e.g., electrodes built into a surface of the pulse generator) or otherwise interact with the pulse generator (e.g., hold the pulse generator extended away from the body to monitor tremors using a motion detector in the pulse generator). In further implementations, one or more sensor outputs may be obtained from external devices, such as a fitness computer, smart watch, or wearable health monitor.

The monitoring used may be based, in part, on a treatment setting. For example, EEG monitoring is easier in a hospital setting, while heart rate monitoring may be achieved by a sensor such as a pulsometer built into the earpiece or another sensor built into a low budget health monitoring device such as a fitness monitoring device or smart watch.

In an illustrative example, feedback related to electrodermal activity could be used to monitor and detect a speed or timing of a symptom and/or therapeutic outcome. In an example, the electrodermal activity could be sensed by electrodes on the therapeutic earpiece device. In another example, the electrodermal activity could be detected by electrodes on another portion of the body and communicated to the system. In some embodiments the electrodermal electrode can be such that it detects specific substances in the skin (e.g., cortisol) via electrochemical means.

In some implementations, the system can further include one or more motion detectors, such as accelerometers or gyroscopes, that can be used gather information to modulate the therapy. In an example, the one or more motion detectors are configured to detect a tremor and/or physiologic movement. In an aspect, the tremor and/or the physiologic movement can be indicative of the underlying condition and/or the treatment to the underlying condition. In an example, the tremor and/or physiologic movement can be indicative of symptoms associated with substance withdrawal. In an aspect, feedback from glucose monitoring can be used to modulate the therapy.

In yet other implementations, EKG can be used to assess heart rate and heart rate variability, to determine the activity of the autonomic nervous system in general and/or the relative activity of the sympathetic and parasympathetic branches of the autonomic nervous system, and to modulate the therapy. Autonomic nervous activity can be indicative of symptoms associated with substance withdrawal. In an aspect, the treatment device can be used to provide therapy for treating cardiac conditions such as atrial fibrillation and heart failure. In an example, therapy can be provided for modulation of the autonomic nervous system. In some implementations, the treatment device can be used to provide therapy to balance a ratio between any combinations of the autonomic nervous system, the parasympathetic nervous system, and the sympathetic nervous system.

In an aspect, the system can monitor impedance measurements allowing closed-loop neurostimulation. In an example, monitoring feedback can be used to alert patient/caregiver if therapy is not being adequately delivered and if the treatment device is removed.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A wearable auricular stimulator, comprising:
   a first flexible body portion adapted to be worn at least partially around an auricle of a wearer, the first flexible body portion comprising
      a skin-facing external side, and
      an internal side opposite the skin-facing external side, the internal side comprising at least one protrusion for supporting a three-dimensional circuitry layout, the at least one protrusion protruding away from the skin-facing external side;
   three-dimensional circuitry on the internal side of the first flexible body portion, wherein the three-dimensional circuitry comprises
      a plurality of conductive traces deposited at least in part on the first flexible body portion, such that at least a portion of the plurality of conductive traces is configured to stretch and/or flex with movement of the first flexible body portion, and
      a plurality of electrodes configured to deliver electrical stimulation therapy to the wearer via the skin-facing external side of the first flexible body portion;
   a plurality of electronic components coupled to the three-dimensional circuitry, wherein
      each electronic component of the plurality of electronic components is electrically coupled with one or more corresponding traces of the plurality of conductive traces and/or one or more corresponding electrodes of the plurality of electrodes of the three-dimensional circuitry,
      the plurality of electronic components comprises two or more elements of different types selected from the group of element types consisting of an illumination element, a processing circuitry element, a physical control element, a communications element, a memory element, and combinations thereof, and
      each electronic component of one or more electronic components of the plurality of electronic components is disposed on or above one or more respective protrusions of the at least one protrusion; and
   a second flexible body portion configured to mate with the first flexible body portion, thereby substantially encapsulating the three-dimensional circuitry and the plurality of electronic components.

2. The wearable auricular stimulator of claim 1, wherein a second one or more-electronic components of the plurality of electronic components are integrated into at least one circuit component, wherein
   coupling the one or more electronic components to the three-dimensional circuitry comprises mounting the at least one circuit component to the internal side of the first flexible body portion.

3. The wearable auricular stimulator of claim 2, wherein the at least one circuit component comprises one or more flex circuits, one or more rigidized flex circuits, and/or one or more rigid-flex circuits.

4. The wearable auricular stimulator of claim 2, wherein the at least one circuit component comprises one or more three-dimensionally formed circuit components comprising one or more bent or curved portions.

5. The wearable auricular stimulator of claim 4, wherein the at least one protrusion comprises at least one set of flexible protrusions, each set of flexible protrusions of the at least one set of flexible protrusions at least partially supporting a respective electronic component of a third one or more electronic components of the plurality of electronic components, wherein
- each set of flexible protrusions provides the respective electronic component with a limited range of motion relative to the first flexible body portion, and
- each set of flexible protrusions is configured to apply a frictional force against movement of the respective electronic component.

6. The wearable auricular stimulator of claim 5, wherein a first set of flexible protrusions of the at least one set of flexible protrusions comprises a plurality of flexible pillars.

7. The wearable auricular stimulator of claim 6, wherein a second set of flexible protrusions of the at least one set of flexible protrusions comprises a second plurality of flexible pillars arranged opposite the plurality of flexible pillars.

8. The wearable auricular stimulator of claim 1, wherein the internal side of the first flexible body portion comprises at least one well, wherein
- each electronic component of a second one or more electronic components of the plurality of electronic components is disposed upon a respective one or more wells of the at least one well.

9. The wearable auricular stimulator of claim 1, wherein the first flexible body portion comprises one or more openings through the first flexible body portion such that at least one surface of each electrode of at least a portion of the plurality of electrodes is exposed for positioning in electrical communication with skin of the wearer proximate the auricle.

10. The wearable auricular stimulator of claim 1, wherein at least one of the first flexible body portion or the second flexible body portion comprises one or more openings such that at least one electronic component of the plurality of electronic components is accessible via at least one respective one of the one or more openings, while the first and second flexible body portions are mated.

11. The wearable auricular stimulator of claim 10, wherein the at least one electronic component comprises a control button or control switch.

12. The wearable auricular stimulator of claim 1, wherein the first flexible body portion is formed as a contiguous molded piece of a single material.

13. The wearable auricular stimulator of claim 1, wherein the first flexible body portion comprises:
- a first section configured for aligning substantially in front of the auricle; and
- a second section configured for aligning substantially against a back of the auricle.

14. The wearable auricular stimulator of claim 13, wherein the plurality of conductive traces of the three-dimensional circuitry comprises a first plurality of conductive traces electrically connecting a portion of the plurality of electronic components disposed in the second section with a portion of the three-dimensional circuitry disposed in the first section.

15. The wearable auricular stimulator of claim 14, wherein the first plurality of conductive traces of the three-dimensional circuitry electrically connect a portion of the plurality of electrodes that is disposed in the second section with at least one of a therapeutic stimulation source of the plurality of electronic components disposed in the first section or a return electrode of the plurality of electrodes disposed in the first section.

16. The wearable auricular stimulator of claim 14, wherein the first flexible body portion further comprises a third section configured to be maintained on at least one of a concha or a cavum of the auricle.

17. The wearable auricular stimulator of claim 16, wherein at least one electrode of the plurality of electrodes is disposed in the third section.

18. The wearable auricular stimulator of claim 13, wherein a first electrode of the plurality of electrodes configured for positioning on, over, or adjacent to a branch of the auriculotemporal nerve (ATN) is disposed in the first section of the first flexible body portion.

19. The wearable auricular stimulator of claim 18, wherein the branch of the ATN is the nervus meatus acustici externi.

20. The wearable auricular stimulator of claim 13, wherein a first electrode of the plurality of electrodes configured for positioning on, over, or in proximity to the auricular branch of the vagus nerve (ABVN) near a point at which the ABVN surfaces through the mastoid canaliculus (MsC) is disposed in the second section of the first flexible body portion.

* * * * *